United States Patent [19]

Buckley, III

[11] Patent Number: 5,600,025

[45] Date of Patent: Feb. 4, 1997

[54] SUBSTANTIALLY STRAIGHT CHAIN ALKYLPHENOLS

[75] Inventor: Thomas F. Buckley, III, Hercules, Calif.

[73] Assignee: Chevron Chemical Company, San Ramon, Calif.

[21] Appl. No.: 246,013

[22] Filed: May 19, 1994

Related U.S. Application Data

[62] Division of Ser. No. 581,345, Sep. 12, 1990, Pat. No. 5,322,529.

[51] Int. Cl.$^6$ .................................................. C07C 39/00
[52] U.S. Cl. ............................................................ 568/716
[58] Field of Search ................................ 568/716; 44/387

[56]  References Cited

U.S. PATENT DOCUMENTS

| | | | |
|---|---|---|---|
| 2,731,416 | 1/1956 | Brandes et al. | 568/716 |
| 3,933,927 | 1/1976 | Goddard | 368/716 |
| 4,514,577 | 4/1985 | Filbey et al. | 568/716 |

OTHER PUBLICATIONS

CA 55: 5421(g); The catalyzed condensation of phenol w/stearone & methyl heptadecyl ketone, 1961.

*Primary Examiner*—Jacqueline V. Howard
*Attorney, Agent, or Firm*—C. J. Caroli

[57]  ABSTRACT

Disclosed are liquid alkylphenyl poly(oxypropylene) aminocarbamates which do not form a wax when cooled to −40° C. in a 50 weight percent solution with toluene, said aminocarbamates having at least one basic nitrogen and an average molecular weight of about 600 to 6,000 and wherein the alkyl group is substantially straight-chain of from 25 to 50 carbon atoms. Also disclosed are fuel compositions and concentrates as well as lubricating oil compositions and concentrates containing said alkylphenyl poly(oxypropylene) aminocarbamates.

5 Claims, No Drawings

SUBSTANTIALLY STRAIGHT CHAIN ALKYLPHENOLS

This is a division of application Ser. No. 07/581,345, filed Sep. 12, 1990, now U.S. Pat. No. 5322,529.

BACKGROUND OF THE INVENTION

Field of the Invention

Numerous deposit-forming substances are inherent in hydrocarbon fuels. These substances when used in internal combustion engines tend to form deposits on and around constricted areas of the engine contacted by the fuel. Typical areas commonly and sometimes seriously burdened by the formation of deposits include carburetor ports, the throttle body and venturies, engine intake valves, etc.

Deposits adversely affect the operation of the vehicle. For example, deposits on the carburetor throttle body and venturies increase the fuel to air ratio of the gas mixture to the combustion chamber thereby increasing the amount of unburned hydrocarbon and carbon monoxide discharged from the chamber. The high fuel-air ratio also reduces the gas mileage obtainable from the vehicle.

Deposits on the engine intake valves when they get sufficiently heavy, on the other hand, restrict the gas mixture flow into the combustion chamber. This restriction, starves the engine of air and fuel and results in a loss of power. Deposits on the valves also increase the probability of valve failure due to burning and improper valve seating. In addition, these deposits may break off and enter the combustion chamber possibly resulting in mechanical damage to the piston, piston rings, engine head, etc.

The formation of these deposits can be inhibited as well as removed by incorporating an active detergent into the fuel. These detergents function to cleanse these deposit-prone areas of the harmful deposits, thereby enhancing engine performance and longevity. There are numerous detergent-type gasoline additives currently available which, to varying degrees, perform these functions.

Three factors complicate the use of such detergent-type gasoline additives. First, with regard to automobile engines that require the use of nonleaded gasolines (to prevent disablement of catalytic converters used to reduce emissions), it has been found difficult to provide gasoline of high enough octane to prevent knocking and the concomitant damage which it causes. The chief problem lies in the area of the degree of octane requirement increase, herein called "ORI", which is caused by deposits formed by the commercial gasoline.

The basis of the ORI problem is as follows: each engine, when new, requires a certain minimum octane fuel in order to operate satisfactorily without pinging and/or knocking. As the engine is operated on any gasoline, this minimum octane increases and, in most cases, if the engine is operated on the same fuel for a prolonged period, will reach an equilibrium. This is apparently caused by an amount of deposits in the combustion chamber. Equilibrium is typically reached after 5,000 to 15,000 miles of automobile operation.

The octane requirement increase in particular engines used with commercial gasolines will vary at equilibrium from 5 to 6 octane units to as high as 12 or 15 units, depending upon the gasoline compositions, engine design and type of operation. The seriousness of the problem is thus apparent. A typical automobile with a research octane requirement of 85, when new, may after a few months of operation require 97 research octane gasoline for proper operation, and little unleaded gasoline of that octane is available. The ORI problem also exists in some degree with engines operated on leaded fuels. U.S. Pat. Nos. 3,144,311; 3,146,203; and 4,247,301 disclose lead-containing fuel compositions having reduced ORI properties.

The ORI problem is compounded by the fact that the most common method for increasing the octane rating of unleaded gasoline is to increase its aromatic content. This, however, eventually causes an even greater increase in the octane requirement. Moreover, some of presently used nitrogen-containing compounds used as deposit-control additives and their mineral oil or polymer carriers may also significantly contribute to ORI in engines using unleaded fuels.

It is, therefore, particularly desirable to provide deposit control additives which effectively control the deposits in intake systems of engines, without themselves eventually contributing to the problem.

In this regard, hydrocarbyl poly(oxyalkylene) aminocarbamates are commercially successful fuel additives which control combustion chamber deposits thus minimizing ORI.

A second complicating factor relates to the low temperature properties of fuel and lubricating oil additives. Since it is not unusual for solutions of these additives to be subjected to cold temperature extremes, it is important that solids (such as waxes) are not formed during handling, storage, or in actual field use. When formed, these waxy constituents can totally plug the in-line filtering devices normally in service in additive distribution systems and the fuel or lube systems of actual operating engines. Such a plugging would obviously be catastrophic and must be avoided.

A third complicating factor relates to the lubricating oil compatibility of the fuel additive. Fuel additives, due to their higher boiling point over gasoline itself, tend to accumulate on surfaces in the combustion chamber of the engine. This accumulation of the additive eventually finds its way into the lubricating oil in the crankcase of the engine via a "blow-by" process and/or via cylinder wall/piston ring "wipe down". In some cases, as much as 25%–30% of the non-volatile fuel components, i.e., including fuel additives, will eventually accumulate in the lubricating oil. Insofar as the recommended drain interval for some engines may be as much as 7,500 miles or more, such fuel additives can accumulate during this interval to substantial quantities in the lubricating oil. In the case where the fuel additive is not sufficiently lubricating oil compatible, the accumulation of such an oil-incompatible fuel additive may actually contribute to crankcase deposits as measured by a Sequence VD test.

The incompatibility of certain fuel additives in lubricating oils, i.e., oils which contain other additives, arises in spite of the fact that some fuel additives are also known to be lubricating oil dispersants. However, even if employed in a fully formulated lubricating oil as a dispersant rather than as a fuel additive, the incompatibility of these dispersants with other additives in the lubricating oil will result in increased crankcase deposits as measured by a Sequence V-D engine test.

Several theories exist as to the cause of the lubricating oil incompatibility of certain fuel/lubricating oil additives. Without being limited to any theory, it is possible that some of these additives when found in the lubricating oil interfere with other additives contained in the lubricating oil and either counterbalance the effectiveness of these additives or actually cause dissolution of one or more of these additives. In either case, the incompatibility of the additive with other additives in the lubricating oil demonstrates itself in less than desirable crankcase deposits as measured by Sequence VD engine tests.

In another theory, when used as a fuel additive, it is possible that the accumulation of the additive into the lubricating oil during the drain interval period surpasses its maximum solubility in the lubricating oil. In this theory, this excess amount of additive is insoluble in the lubricating oil and is what causes increased crankcase deposits.

In still another theory, it is possible that the additive will decompose in the lubricating oil during engine operation and the decomposition products are what cause increased crankcase deposits.

In any case, lubricating oil incompatible additives are less than desirable insofar as their use during engine operation will result in increased deposits in the crankcase. This problem can be catastrophic.

It is recognized that hydrocarbyl poly(oxybutylene) aminocarbamates are substantially more expensive than the hydrocarbyl poly(oxypropylene) aminocarbamates. This is because butylene oxide is more expensive than propylene oxide. However, because heretofore no known hydrocarbyl poly(oxypropylene) aminocarbamate was found to be sufficiently lubricating oil compatible and non-waxy, it was necessary to employ the more expensive hydrocarbyl poly(oxybutylene) aminocarbamates which are sufficiently lubricating oil compatible. Accordingly, it would be particularly advantageous to develop hydrocarbyl poly(oxypropylene) aminocarbamates which are compatible in lubricating oil compositions and are non-waxy at −40° C.

The instant invention is directed to lubricating oil compositions and fuel compositions containing a novel class of hydrocarbyl poly(oxypropylene) aminocarbamates. As a fuel additive, these novel hydrocarbyl poly(oxyalkylene) aminocarbamates control combustion chamber deposits thus minimizing ORI and in lubricating oil are compatible with the lubricating oil composition. As a lubricating oil additive, these novel hydrocarbyl poly(oxyalkylene) aminocarbamates provide dispersancy without possessing lubricating oil incompatibility. Significantly, the novel additives of this invention are also liquids which do not form a wax at −40° C. in a 50 weight percent solution with toluene.

Relevant Art

Numerous references disclose hydrocarbyl poly(oxyalkylene) aminocarbamates as fuel additives. These include the following U.S. Pat. Nos.:

4,160,648; 4,243,798; 4,521,610; and 4,191,537; 4,270,930; 4,568,358 4,197,409; 4,274,837; 4,236,020; 4,288,612;

Of particular relevance is U.S. Pat. No. 4,274,837 which discloses that hydrocarbyl poly(oxyalkylene) aminocarbamates containing certain poly(oxyalkylene) chains, i.e., oxypropylene, when used in fuels employed in combination with certain lubricating oils, produce crankcase varnish. This reference further discloses that lubricating oil compatible hydrocarbyl poly(oxypropylene) aminocarbamates are improved by employing the poly(oxypropylene) as a copolymer also containing 1 to 5 branched $C_9$ to $C_{30}$ oxyalkylene units.

U.S. Pat. No. 4,160,648 discloses an intake system deposit control additive for fuels which is hydrocarbyl poly(oxyalkylene) aminocarbamate wherein the hydrocarbyl is from 1 to 30 carbon atoms including alkyl or alkylphenyl groups. Specifically disclosed hydrocarbyl groups include tetrapropenylphenyl, olelyl and a mixture of $C_{16}$, $C_{18}$ and $C_{20}$ alkyl groups. Likewise, U.S. Pat. No. 4,288,612 discloses deposit control additives for gasoline engines which are hydrocarbyl poly(oxyalkylene) aminocarbamates wherein the hydrocarbyl group contains from 1 to about 30 carbon atoms including alkylphenyl groups wherein the alkyl group is straight or branched chain of from 1 to about 24 carbon atoms. U.S. Pat. No. 4,568,358 discloses diesel fuel compositions containing an additive such as a hydrocarbyl poly(oxyalkylene) aminocarbamate. This reference discloses hydrocarbyl groups such as alkyl groups of 1 to 30 carbon atoms; aryl groups of 6 to 30 carbon atoms, alkaryl groups of 7 to 30 carbon atoms, etc.

U.S. Pat. No. 4,332,595 discloses hydrocarbyl poly(oxyalkylene) polyamines wherein the hydrocarbyl group is a hydrocarbyl radical of 8 to 18 carbon atoms derived from linear primary alcohols.

U.S. Pat. Nos. 4,233,168 and 4,329,240 among others disclose lubricating oil compositions containing a dispersant amount of a hydrocarbyl poly(oxyalkylene) aminocarbamate.

While these prior art references disclose fuel compositions containing $C_1$ to $C_{30}$ hydrocarbyl poly(oxyalkylene) aminocarbamates which include poly(oxypropylene) polymers, none of these references disclose the unique hydrocarbyl group of this invention nor do any of these references suggest that use of this unique hydrocarbyl group would overcome the art recognized problem of lubricating oil incompatibility arising from using the prior art hydrocarbyl poly(oxypropylene) aminocarbamates, and especially the problem of low temperature wax formation.

SUMMARY OF THE INVENTION

The present invention provides a liquid alkylphenyl poly(oxypropylene) aminocarbamate which does not form a wax when cooled to −40° C. in a 50 weight percent solution with toluene, said aminocarbamate having at least one basic nitrogen and an average molecular weight of about 600 to 6,000 and wherein the alkyl group of said alkylphenyl poly(oxypropylene) aminocarbamate is a substantially straight-chain alkyl group of from about 25 to 50 carbon atoms.

In a composition aspect, the instant invention is directed toward a fuel composition containing a novel class of hydrocarbyl poly(oxypropylene) aminocarbamates which as a fuel additive controls combustion chamber deposits thus minimizing ORI and in lubricating oil is compatible with the lubricating oil composition. In particular, the instant invention is directed toward a fuel composition comprising a hydrocarbon boiling in the gasoline or diesel range and from about 30 to about 5,000 parts per million of the alkylphenyl poly(oxypropylene) aminocarbamate of the present invention.

In another composition aspect, the instant invention is directed to a fuel concentrate comprising an inert stable oleophilic organic solvent boiling in the range of 150° to 400° F. and from 5 to 50 weight percent of an alkylphenyl poly(oxypropylene) aminocarbamate of this invention.

In still another composition aspect, the instant invention is directed to a lubricating oil composition comprising an oil of lubricating viscosity and a dispersant effective amount of an alkylphenyl poly(oxypropylene) aminocarbamate of this invention.

In still another composition aspect, the instant invention is directed to a lubricating oil concentrate comprising from about 90 to 50 weight percent of an oil of lubricating viscosity and from about 10 to 50 weight percent of an alkylphenyl poly(oxypropylene) aminocarbamate of this invention.

The present invention also relates to the novel alkylphenol compounds which are employed to prepare the instant alkylphenyl poly(oxypropylene) aminocarbamates. These novel alkylphenol intermediate compounds are alkylphenols wherein the alkyl group is a substantially straight-chain alkyl group of from about 25 to 50 carbon atoms and is attached to the phenol ring at least 6 carbon atoms from the terminus of the longest chain of the alkyl group. Preferably, the alkyl group on the alkylphenol will contain from about 28 to 50 carbon atoms, and more preferably, from about 30 to 45 carbon atoms. Moreover, the alkyl substituent is preferably derived from a substantially straight chain alpha olefin oligomer of $C_8$ to $C_{20}$ alpha olefins.

Among other factors, the present invention is based on the discovery that the "pinwheel" alklphenyl poly(oxypropylene) aminocarbamates of the present invention having a substantially straight chain alkyl substituent do not produce wax when cooled to $-40°$ C. in a 50 wt % solution of toluene. These non-waxy carbamates do not produce any traces of crystalline wax under these conditions.

It is critical that these aminocarbamates are non-waxy at low temperatures. Fuel additives and lubricating oil additives must all be able to be pumped, for example, into fuels, and to operate effectively under cold conditions in such locations as Alaska or Wisconsin in the wintertime.

Even very small amounts of wax, e.g., milligrams, will plug the micron-sized filters that these additives commonly come in contact with. For example, there are micron-sized filters in the additive distribution and blending systems which make additive packages and blends prior to the consumer's purchase. There are also micron-sized filters in automobiles and diesel engines where the fuel is filtered prior to combustion.

DETAILED DESCRIPTION OF THE INVENTION

The alkylphenyl poly(oxypropylene) aminocarbamates of the present invention consist of an amino moiety and an alkylphenyl poly(oxypropylene) polymer bonded through a carbamate linkage, i.e., —OC(O)N<. The specific alkylphenyl group employed in the instant invention in the alkylphenyl poly(oxypropylene) polymer is critical to achieving lubricating oil compatibility for the alkylphenyl poly(oxypropylene) aminocarbamates, while providing excellent low temperature properties. In particular, it has been found that employing the "pinwheel" alkylphenyl group of this invention wherein the alkyl group is substantially straight-chain of from 25 to 50 carbon atoms results in an alkylphenyl poly(oxypropylene) aminocarbamate which is lubricating oil compatible and non-waxy at low temperatures.

As used herein, the abbreviation "PO" is meant to designate propylene oxide or propylene oxide-derived polymers. Similarly, the abbreviation "BO" is meant to designate butylene oxide or butylene oxide-derived polymers. Also, the term "EDA" is meant to designate ethylene diamine or ethylene diamine-derived carbamates.

Further, the term "DETA" is meant to designate diethylene triamine or diethylene triamine-derived carbamates.

The term "alpha olefin" or "simple alpha olefin" as used herein refers generally to 1-olefins, wherein the double bond is at the terminal position of an alkyl chain. Alpha olefins are almost always mixtures of isomers and often also mixtures of compounds with a range of carbon numbers. Low molecular weight alpha olefins, such as the $C_6$, $C_8$, $C_{10}$, $C_{12}$ and $C_{14}$ alpha olefins, are almost exclusively 1-olefins. Higher molecular weight olefin cuts such as $C_{16-18}$, or $C_{20-24}$ have increasing proportions of the double bond isomerized to an internal or vinylidene position; nonetheless these higher molecular weight cuts are also called alpha olefins herein.

The term "alpha olefin oligomer(s)" (AOO), as used herein means olefin dimers, trimers, tetramers and pentamers prepared or derived from $C_8$ to $C_{20}$ alpha olefins. These AOO's have a pinwheel-type structure consisting of primarily internal disubstituted and trisubstituted olefins. The olefin double bond of these AOO's is generally located at least n-2 carbon atoms from the end of the longest continuous carbon chain, where n is the number of carbon atoms in the starting alpha olefin.

The Alkyl Substituent

The alkyl substituent of the alkyphenyl moiety of the present alkylphenyl poly(oxpropylene) carbamates is a substantially straight-chain alkyl group having from about 25 to 50 carbon atoms. The term "substantially straight-chain" is meant to designate an alkyl group wherein greater than about 80 number percent of the individual carbon atoms in the alkyl substituent are either primary ($CH_3$—) or secondary (—$CH_2$—) carbon atoms. Preferably, greater than 85 number percent of the carbon atoms in the alkyl substituent are primary or secondary carbons.

The alkyl substituent in the alkylphenyl poly(oxypropylene) aminocarbamates of the present invention is arranged in what will herein be designated as a "pinwheel" configuration. This configuration has been found to be critical to providing aminocarbamates having non-waxy low temperature characteristics.

By "pinwheel" configuration is meant that the alkyl group is attached, for example to an aromatic ring, at a position significantly removed from the terminus of the longest chain of the alkyl group. This results in at least two hydrocarbon tails, or wheels of the pinwheel, emanating from near the attachment point. By "significantly removed from the terminus" is meant at least 6 carbon atoms from the terminus of the longest chain of the alkyl group, preferably at least 8 carbon atoms toward the center of the chain. Thus a "pinwheel" alkyl phenol has an alkyl group comprising at least two tails of at least six carbon atoms in length, preferably at least 8 carbon atoms in length.

Preferred "pinwheel" compounds useful in this invention are those wherein the alkyl substituent has tails which are substantially straight-chain hydrocarbon radicals.

As will be discussed in more detail below, the alkylphenyl substituent of the aminocarbamate of this invention is derived from the corresponding alkylphenol. A preferred type of alkylphenol is that prepared by alkylating phenol with one or more alpha olefin oligomers. Alkylation with alpha olefin oligomers, such as decene trimer or octene tetramer, provides alkylphenols having "pinwheel" configurations. Such configurations can be represented by structure A as an example of decene trimer-derived alkylphenol and structure B as an example of octene tetramer-derived alkylphenol, as shown below. In these structures, the brackets are intended to denote the various manners of attachment of the alkyl group to the phenol.

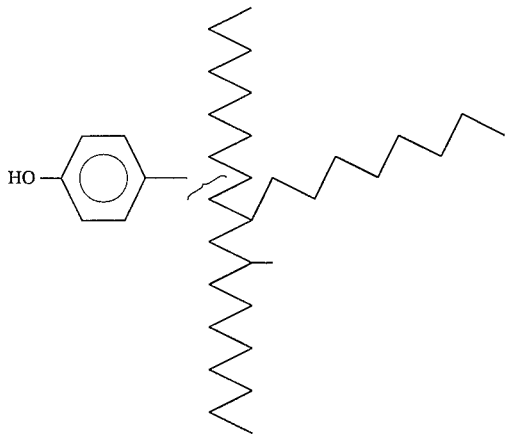

A

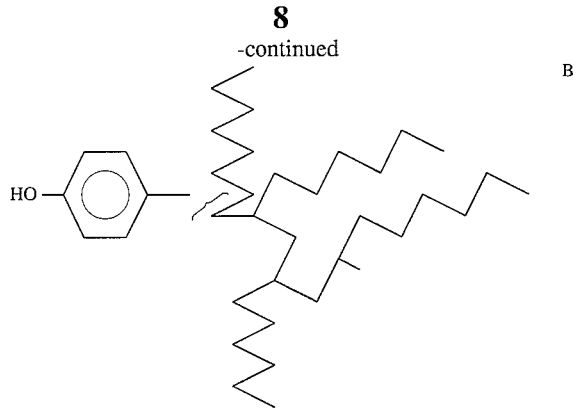

B

The alpha olefin oligomers used herein are prepared by methods well-known in the art. One preferred method of preparing these oligomers is using $BF_3$ as the oligomerization catalyst, as described, for example, in U.S. Pat. Nos. 4,238,343 and 4,045,507, and in Onopchenko, et al., *$BF_3$-Catalyzed Oligomerization of Alkenes (Structures, Mechanisms and Properties)*. 183rd ACS Natl. Meet. (Las Vegas, March 1982). Ind. Eng. Chem., Prod. Res. Dev., 22(2), 182–91 (June 1983).

These alpha olefin oligomers are 75% or more di or trisubstituted at the olefin site. For example, an alpha olefin trimer has a structure that can be represented by:

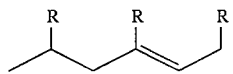

wherein:

R=n–2, and n is the carbon number of the starting alpha olefin.

Alpha olefin oligomers are substantially straight-chain with respect to the number of branched (i.e., tertiary or quartemary) carbons as a percent of the total number of carbon atoms. That is, greater than 80 percent of the carbon atoms in the molecule are primary or secondary carbons, preferably greater than 85 percent.

Substantially straight-chain alkyl groups are exemplified in Table A below:

TABLE A

ALKYLPHENOLS

| Starting Olefin | Representative Phenol Structure | $A^{(1)}$ | $B^{(2)}$ | Total A & B | Percent[3] Primary & Secondary |
|---|---|---|---|---|---|
| Propylene Tetramer (Comparative) | *(structure: p-alkylphenol with branched propylene tetramer chain)* | 8 | 4 | 12 | 66 |
| $C_{30}$ Decene Trimer | *(structure: p-alkylphenol with pinwheel chain, three R branches, Where R is linear $C_8$)* | 27 | 3 | 30 | 90 |
| $C_{32}$ Octene Tetramer | *(structure: p-alkylphenol with pinwheel chain, four R branches, Where R is linear $C_6$)* | 28 | 4 | 32 | 83 |

[1] A = Primary & Secondary Alkyl Carbon Atoms
[2] B = Tertiary & Quarternary Alkyl Carbon Atoms
[3] $\dfrac{A}{A \& B}$, %

Preferred alpha olefin oligomers (AOO's) are derived from $C_8$ to $C_{20}$ alpha olefins, more preferably, $C_{10}$ to $C_{16}$ alpha olefins. Preferred AOO's are dimers, trimers, tetramers and pentamers. Preferably, the alkyl group of the instant carbamates is derived from alpha olefin oligomers selected from the group consisting of: $C_8$ tetramers, $C_{10}$ trimers, $C_{12}$ trimers, $C_{14}$ dimers and trimers, $C_{16}$ dimers and trimers, $C_{18}$ dimers and $C_{20}$ dimers.

As described above, the alkyl substituent of the present alkylphenyl poly(oxypropylene) aminocarbamates is arranged in a so-called "pinwheel" configuration. This "pinwheel" configuration is readily distinguishable from alkyl groups wherein the hydrocarbon chains are attached at or near the terminus of the longest chain of the alkyl group, i.e., within 1 to 5 carbon atoms of a terminus. Thus, aminocarbamates prepared from simple alpha olefins, (as compared to alpha olefin oligomers) as well as their precursors, including the phenols and the alkylphenyl poly(oxypropylene) alcohols, have alkyl groups in a "terminal" configuration. Compounds having an alkyl group in a terminal configuration are herein designated "terminal compounds", for example, $C_{20-24}$ terminal alkyl phenols and terminal alkyl carbamates.

In terminal compounds such as terminal alkyl phenols, there is only 1 main chain emanating from near the attachment point of the alkyl group to the phenol. Terminal compounds include those prepared by reacting alpha olefins with phenol under typical acidic reaction conditions.

The Preferred Alkyphenyl Group

The preferred alkylphenyl group of the alkylphenyl poly(oxypropylene) aminocarbamate employed in this invention is derived from the corresponding alkylphenol of Formula I below:

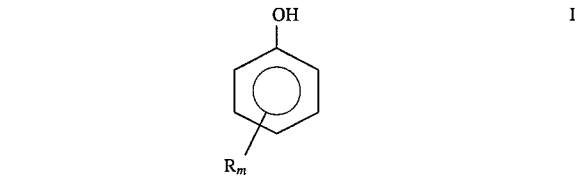

wherein R is a substantially straight-chain alkyl group of from about 25 to 50 carbon atoms and m is an integer from 1 to 2.

Preferably, R is a substantially straight-chain alkyl group of from 28 to 50 carbon atoms. More preferably, R is a substantially straight-chain alkyl group of from 30 to 45 carbon atoms.

When m is one, the alkylphenyl is a monoalkylphenyl; whereas when m is two, the alkylphenyl is a dialkylphenyl.

The alkylphenols of Formula I above are prepared by reacting the appropriate olefin or olefin mixture with phenol in the presence of an alkylating catalyst at a temperature of from about 60° C. to 200° C., and preferably 125° C. to 180° C. either neat or in an essentially inert solvent at atmospheric pressure. A preferred alkylating catalyst is a sulfonic acid catalyst such as Amberlyst 15® available from Rohm and Haas, Philadelphia, Pa. Molar ratios of reactants can be employed. When molar ratios are employed, the reaction yields a mixture of dialkylphenol, monoalkylphenol and unreacted phenol. As noted above, dialkylphenol and monoalkylphenol can be used to prepare the additives used in the compositions of this invention whereas the unreacted phenol is preferably removed from the post reaction mixture via conventional techniques. Alternatively, molar excess of phenol can be employed, i.e., 2 to 2.5 equivalents of phenol for each equivalent of olefin with unreacted phenol recycled. The latter process maximizes monoalkylphenol. Examples of inert solvents include benzene, toluene, chlorobenzene and 250 thinner which is a mixture of aromatics, paraffins and naphthenes.

The preferred alkylphenyl group is derived from a pinwheel phenol. Pinwheel phenols may be prepared from alpha olefin oligomers.

Useful AOO derived alkylphenols have average molecular weights in the range of 480 to 790, and average alkyl carbon numbers ranging from 25 to 50, and preferably from 28 to 50. More preferred average alkyl carbon numbers are in the range of from 30 to 45.

Alternative methods of preparing the alkylphenol compounds used herein are also contemplated. "Pinwheel" alkyl phenols can be synthesized by any number of methods. These methods typically rely upon either preforming the entire alkyl moiety prior to alkylation of the phenol or subsequently elaborating a preformed alkyphenol wherein the alkyl group has the requisite functionality for further development to a pinwheel alkyl phenol. Thus, one could alkylate phenol with either a pinwheel olefin or a corresponding alcohol, or alkyl halide, such as a chloride or bromide.

The exact structure of the final alkyl phenol is difficult to predict with certainty. Alkylations using carbonium ions result in rearrangements during carbonium ion formation and reaction. It is also known that the products of such alkylation schemes can also suffer rearrangements, dealkylations, and realkylations under reaction conditions. Thus, a variety of structures are included in the present invention.

Particularly preferred monoalkylphenols employed in this invention are either ortho-monoalkylphenols of Formula II below:

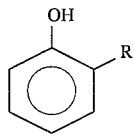

II or para-monoalkylphenols of Formula III below:

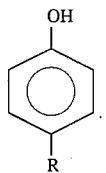

III

Particularly preferred dialkylphenols employed in this invention are generally 2,4-dialkylphenols of Formula IV below:

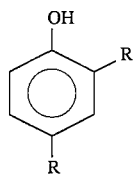

IV although there may be minor amounts of 2,6-dialkylphenol of Formula V below:

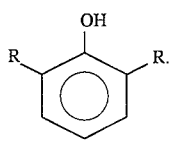

V

Preferred Poly(oxypropylene) Component

The alkylphenyl poly(oxypropylene) polymers which are utilized in preparing the carbamates of the present invention are monohydroxy compounds, i.e., alcohols, often termed alkylphenyl "capped" poly(oxypropylene) glycols and are to be distinguished from the poly(oxypropylene) glycols (diols), which are not alkylphenyl terminated, i.e., not capped. The alkylphenyl poly(oxypropylene) alcohols are produced by the addition of propylene oxide to the alkylphenol of Formula I, i.e.,

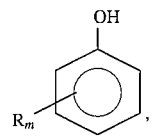

I under polymerization conditions, wherein R and m are as defined above. In general, the poly(oxypropylene) polymers will vary in chain length but their properties closely approximate those of the polymer represented by the average composition and molecular weight. Each poly(oxypropylene) polymer contains at least 1 oxypropylene unit, preferably from 1 to about 100 oxypropylene units, more preferably from about 5 to about 50 oxypropylene units, and most preferably from about 10 to about 25 oxypropylene units. Methods of production and properties of these polymers are disclosed in U.S. Pat. Nos. 2,841,479 and 2,782,240, which are incorporated herein by reference, as well as Kirk-Othmer's "Encyclopedia of Chemical Technology", Volume 19, p. 507. An alternative method for preparing alkylphenyl poly(oxypropylene) polymers having either 1, 2, or 3 oxypropylene units involves employing a compound of Formula VI below

VI wherein q is an integer from 1 to 3. When employing the compound of Formula VI, the phenoxide of the alkylphenol, I, is first prepared and then reacted with the compound of Formula VI to yield the desired alkylphenyl poly(oxypropylene) polymer having from 1 to 3 oxypropylene units. Compounds of Formula VI are commercially available or can be prepared by art recognized methods.

Preferred Amine Component

The amine moiety of the alkylphenyl poly(oxypropylene) aminocarbamate employed in this invention is preferably derived from a polyamine having from 2 to about 12 amine nitrogen atoms and from 2 to about 40 carbon atoms. The polyamine is preferably reacted with an alkylphenyl poly(oxypropylene) chloroformate to produce the alkylphenyl poly(oxypropylene) aminocarbamate additives finding use within the scope of the present invention. The chloroformate is itself derived from alkylphenyl poly(oxypropylene) alcohol by reaction with phosgene. The polyamine, encompassing diamines, provides the product alkylphenyl poly(oxypropylene) aminocarbamate with, on average, at least about one basic nitrogen atom per carbamate molecule, i.e., a nitrogen atom titratable by a strong acid. The polyamine preferably has a carbon-to nitrogen ratio of from about 1:1 to about 10:1.

The polyamine may be substituted with substituents selected from (A) hydrogen, (B) hydrocarbyl groups of from 1 to about 10 carbon atoms, (C) acyl groups of from 2 to about 10 carbon atoms, and (D) monoketo, monohydroxy, mononitro, monocyano, lower alkyl and lower alkoxy derivatives of (B) and (C). "Lower", as used in terms like lower alkyl or lower alkoxy, means a group containing from 1 to about 6 carbon atoms. At least one of the substituents on one of the basic nitrogen atoms of the polyamine is hydrogen, e.g., at least one of the basic nitrogen atoms of the polyamine is a primary or secondary amino nitrogen atom.

Hydrocarbyl, as used in describing all the components of this invention, denotes an organic radical composed of carbon and hydrogen which may be aliphatic, alicyclic, aromatic or combinations thereof, e.g., aralkyl. Preferably, the hydrocarbyl group will be relatively free of aliphatic unsaturation, i.e., ethylene and acetylenic, particularly acetylenic unsaturation. The substituted polyamines of the present invention are generally, but not necessarily, N-substituted polyamines. Exemplary hydrocarbyl groups and substituted hydrocarbyl groups include alkyls such as methyl, ethyl, propyl, butyl, isobutyl, pentyl, hexyl, octyl, etc., alkenyls such as propenyl, isobutenyl, hexenyl, octenyl, etc., hydroxyalkyls, such as 2-hydroxyethyl, 3-hydroxypropyl, hydroxyisopropyl, 4-hydroxybutyl, etc., ketoalkyls, such as 2-ketopropyl, 6-ketooctyl, etc., alkoxy and lower alkenoxy alkyls, such as ethoxyethyl, ethoxypropyl, propoxyethyl, propoxypropyl, 2-(2ethoxyethoxy)ethyl, 2-(2-(2-ethoxyethoxy)ethoxy)ethyl, 3,6,9,12-tetraoxatetradecyl, 2-(2-ethoxyethoxy)hexyl, etc.

The acyl groups of the aforementioned (C) substituents are such as propionyl, acetyl, etc. The more preferred substituents are hydrogen, $C_1$–$C_4$ alkyls and $C_1$–$C_4$ hydroxyalkyls.

In a substituted polyamine the substituents are found at any atom capable of receiving them. The substituted atoms, e.g., substituted nitrogen atoms, are generally geometrically inequivalent, and consequently the substituted amines finding use in the present invention can be mixtures of mono- and polysubstituted polyamines with substituent groups situated at equivalent and/or inequivalent atoms.

The more preferred polyamine finding use within the scope of the present invention is a polyalkylene polyamine, including alkylene diamine, and including substituted polyamines, e.g., alkyl and hydroxyalkyl-substituted polyalkylene polyamine. Preferably, the alkylene group contains from 2 to 6 carbon atoms, there being preferably from 2 to 3 carbon atoms between the nitrogen atoms. Such groups are exemplified by ethylene, 1,2-propylene, 2,2-dimethyl-propylene trimethylene, 1,3,2-hydroxypropylene, etc. Examples of such polyamines include ethylene diamine, diethylene triamine, di(trimethylene)triamine, dipropylene triamine, triethylene tetramine, tripropylene tetramine, tetraethylene pentamine, and pentaethylene hexamine. Such amines encompass isomers such as branched-chain polyamines and the previously mentioned substituted polyamines, including hydroxy- and hydrocarbyl-substituted polyamines. Among the polyalkylene polyamines, those containing 2–12 amine nitrogen atoms and 2–24 carbon atoms are especially preferred, and the $C_2$–$C_3$ alkylene polyamines are most preferred, in particular, the lower polyalkylene polyamines, e.g., ethylene diamine, diethylene triamine, propylene diamine, dipropylene triamine, etc.

The amine component of the alkylphenyl poly(oxypropylene) aminocarbamate also may be derived from heterocyclic polyamines, heterocyclic substituted amines and substituted heterocyclic compounds, wherein the heterocycle comprises one or more 5–6 membered rings containing oxygen and/or nitrogen. Such heterocycles may be saturated or unsaturated and substituted with groups selected from the aforementioned (A), (B), (C) and (D). The heterocycles are exemplified by piperazines, such as 2-methylpiperazine, N-(2-hydroxyethyl)piperazine, 1,2bis-(N-piperazinyl)-ethane, and N,N'bis(N-piperazinyl)piperazine, 2-methylimidazoline, 3-aminopiperidine, 2-aminopyridine, 2-(3-aminoethyl)3-pyrroline, 3-aminopyrrolidine, N-(3-aminopropyl)morpholine, etc. Among the heterocyclic compounds, the piperazines are preferred.

Another class of suitable polyamines are diaminoethers represented by Formula VII

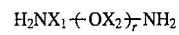   VII wherein $X_1$ and $X_2$ are independently alkylene from 2 to about 5 carbon atoms and r is an integer from 1 to about 10. Diamines of Formula VII are disclosed in U.S. Pat. No. 4,521,610, which is incorporated herein by reference for its teaching of such diamines.

Typical polyamines that can be used to form the compounds of this invention by reaction with a poly(oxyalkylene)chloroformate include the following:

ethylene diamine, 1,2-propylene diamine, 1,3-propylene diamine, diethylene triamine, triethylene tetramine, hexamethylene diamine, tetraethylene pentamine, dimethylaminopropylene diamine, N-(beta-aminoethyl)-piperazine, N-(beta-aminoethyl)piperidine, 3-amino-N-ethylpiperidine, N-(beta-aminoethyl)morpholine, N,N'-di(beta-aminoethyl)piperazine, N,N'-di(beta-aminoethylimidazolidone-2; N-(beta-cyano-ethyl)ethane-1,2-diamine, 1-amino-3,6,9-triazaoctadecane, 1-amino-3,6-diaza-9-oxadecane, N-(beta-aminoethyl)diethanol-amine, N'-acetyl-N-methyl-N-(beta-aminoethyl)ethane-1,2-diamine, N-acetonyl-1,2-propanediamine, N-(beta-nitroethyl)-1,3-propane diamine, 1,3-dimethyl-5(beta-aminoethyl)hexahydrotriazine, N-(beta-aminoethyl)hexahydrotriazine, 5-(beta-aminoethyl)-1,3,5-dioxazine, 2-(2-aminoethylamino)-ethanol, 2[2-(2-aminoethylamino)ethylamino]-ethanol.

The amine component of the alkylphenyl poly(oxypropylene) aminocarbamate may also be derived from an amine-containing compound which is capable of reacting with an alkylphenyl poly(oxypropylene) alcohol to produce an alkylphenyl poly(oxypropylene) aminocarbamate having at least one basic nitrogen atom. For example, a substituted aminoisocyanate, such as $(R)_2NCH_2CH_2NCO$, wherein R is, for example, a hydrocarbyl group, reacts with the alcohol to produce the aminocarbamate additive finding use within the scope of the present invention. Typical aminoisocyanates that may be used to form the fuel additive compounds of this invention by reaction with a hydrocarbylpoly(oxyalkylene) alcohol include the following: N,N-(dimethyl)aminoisocyanatoethane, generally, N,N-(dihydrocarbyl)aminoisocyanatoalkane, more generally, N-(perhydrocarbyl)-isocyanato-pol-olyalkylene polyamine, N,N-(dimethyl)aminoisocyanatobenzene, etc.

In many instances the amine used as a reactant in the production of the carbamate of the present invention is not a single compound but a mixture in which one or several compounds, predominate with the average composition indicated. For example, tetraethylene pentamine prepared by the polymerization of aziridine or the reaction of dichloroethylene and ammonia will have both lower and higher amine members, e.g., triethylene tetramine, substituted piperazines and pentaethylene hexamine, but the composition will be mainly tetraethylene pentamine and the empirical formula of the total amine composition will closely approximate that of tetraethylene pentamine. Finally, in preparing the compounds of this invention, where the various nitrogen atoms of the polyamine are not geometrically equivalent, several substitutional isomers are possible and are encompassed within the final product. Methods of preparation of amines, isocyanates and their reactions are detailed in Sidgewick's "The Organic Chemistry of Nitrogen", Clarendon Press, Oxford, 1966; Nollers' "Chemistry of Organic Compounds", Saunders, Philadelphia, 2nd Ed. 1957; and Kirk-Othmer's "Encyclopedia of Chemical Technology", 3rd Ed., especially Volume 2, pp. 272–375.

Preferred Alkylphenyl Poly(oxypropylene) Aminocarbamate

Having described the preferred alkylphenyl poly(oxypropylene) component and the preferred polyamine component, the preferred alkylphenyl poly(oxypropylene) aminocarbamate additive of the present invention is obtained by linking these components together through a carbamate linkage i.e.,

wherein the ether oxygen may be regarded as the terminal hydroxyl oxygen of the alkylphenyl poly(oxypropylene) alcohol component, and the carbonyl group —C(O)— is preferably provided by the coupling agent, e.g., phosgene.

The alkylphenyl poly(oxypropylene) aminocarbamate employed in the present invention has at least one basic nitrogen atom per molecule. A "basic nitrogen atom" is one that is titratable by a strong acid, e.g., a primary, secondary, or tertiary amino nitrogen, as distinguished from, for example, an amido nitrogen, i.e.,

which is not so titratable. Preferably, the basic nitrogen is in a primary or secondary amino group.

The preferred alkylphenyl poly(oxypropylene) aminocarbamate has an average molecular weight of from about 600 to 6,000; preferably an average molecular weight of from 800 to 3,000; and most preferably an average molecular weight of from 1,000 to 2,500.

A preferred class of alkylphenyl poly(oxypropylene) aminocarbamate can be described by the following general formula:

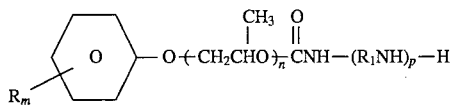

wherein R is a substantially straight-chain alkyl group of from about 25 to 50 carbon atoms; $R_1$ is alkylene of 2 to 6 carbon atoms; m is an integer from 1 to 2; n is an integer such that the molecular weight of the compound is from about 600 to 6,000; and p is an integer from 1 to about 6; and wherein said compound does not form a wax when cooled to −40° C. in a 50 weight percent solution with toluene. Preferably, R is attached to the phenyl ring at least 6 carbon atoms from the terminus of the longest chain of said alkyl group R.

Hydrophilic-Lipophilic Balance

It is important that the relatively hydrophilic propylene oxide polymeric back-bone be balanced by the hydrophobic alkyl carbons of the alkyl phenol. The aminocarbamates of this invention must achieve a good hydrophilic-lipophilic balance (HLB) in order to have sufficient hydrocarbon solubility in oil and therefore to not perform detrimentally with regard to crankcase varnish.

For good lubricant solubility, It has been found that the ratio of the number of carbon atoms in the alkyl group needs to be about twice the number of propylene oxide units. For example, if the average number of propylene oxide units is n, then the alkyl chain attached to the phenoxy radical should have approximately 2n carbon atoms; preferably, between 2n−4 and 2n+4 carbon atoms; most preferably between 2n and 2n+4 carbon atoms.

Preparation of the Alkylphenyl Poly(oxypropylene) Aminocarbamate

The additives employed in this invention can be most conveniently prepared by first reacting the appropriate alkylphenyl poly(oxypropylene) alcohol with phosgene to produce an alkylphenyl poly(oxypropylene) chloroformate. The chloroformate is then reacted with the polyamine to produce the desired alkylphenyl poly(oxypropylene) aminocarbamate.

Preparation of aminocarbamates are disclosed in U.S. Pat. Nos. 4,160,648; 4,191,537; 4,197,409; 4,236,020; 4,243,798; 4,270,930; 4,274,837; 4,288,612; 4,512,610; and 4,568,358, which are incorporated wherein by reference. In general, the reaction of the poly(oxypropylene) compound and phosgene is usually carried out on an essentially equimolar basis, although excess phosgene can be used to improve the degree of reaction. The reaction may be carried out a temperatures from −10° to 100° C., preferably in the range of 0° to 50° C. The reaction will usually be complete within ¼ to 5 hours. Times of reaction will usually be in the range of from 2 to 4 hours.

A solvent may be used in the chloroformylation reaction. Suitable solvents include benzene, toluene, etc.

The reaction of the resultant chloroformate with the amine may be carried out neat or preferably in solution. Temperatures of from −10° to 200° C. may be utilized, the desired product may be obtained by water wash and stripping usually be the aid of vacuum, of any residual solvent.

The mole ratio of polyamine to polyether chloroformate will generally be in the range from about 2 to 20 moles of polyamine per mole of chloroformate, and more usually 5 to 15 moles of polyamine per mole of chloroformate. Since suppression of polysubstitution of the polyamino is usually desired, large molar excesses of the polyamine will be used. Additionally, the preferred adduct is the monocarbamate compound, as opposed to the bis(carbamate) or disubstituted aminoether.

The reaction or reactions may be conducted with or without the presence of a reaction solvent. A reaction solvent is generally employed whenever necessary to reduce the viscosity of the reaction product. These solvents should be stable and inert to the reactants and reaction product. Depending on the temperature of the reaction, the particular chloroformate used, the mole ratios, as well as the reactant concentrations, the reaction time may vary from less than 1 minute to 3 hours.

After the reaction has been carried out for a sufficient length of time, the reaction mixture may be subjected to extraction with a hydrocarbon-water or hydro-carbon-alcohol-water medium to free the product from any low-molecular-weight amine salts which have formed and any unreacted diamine. The product may then be isolated by evaporation of the solvent. Further purification may be effected by column chromatography on silica gel.

Depending on the particular application of the composition of this invention, the reaction may be carried out in the medium in which it will ultimately find use, e.g., polyether carriers or an oleophilic organic solvent or mixtures thereof and be formed at concentrations which provide a concentrate of a detergent composition. Thus, the final mixture may be in a form to be used directly for blending in fuels.

An alternative process for preparing the alkylphenyl poly(oxypropylene) aminocarbamates employed in this invention involves the use of an arylcarbonate intermediate. That is to say, the alkylphenyl poly(oxypropylene) alcohol is reacted with an aryl chloroformate to form an arylcarbonate which is then reacted with the polyamine to form the aminocarbamate employed in this invention. Particularly useful aryl chloroformates include phenyl chloroformate, p-nitrophenyl chloroformate, 2,4-dinitrophenyl chloroformate, p-chlorophenyl chloroformate, 2,4-dichlorophenyl chloroformate, and p-trifluoromethylphenyl chloroformate. Use of the aryl carbonate intermediate allows for conversion to aminocarbamates containing close to the theoretical basic nitrogen while employing less excess of polyamine, i.e., molar ratios of generally from 1:1 to about 5:1 of polyamine to the arylcarbonate, and additionally avoids the generation of hydrogen chloride in the reaction forming the aminocarbamate. Preparation of hydrocarbyl capped poly(oxyalkylene) aminocarbamates via an arylcarbonate intermediate are disclosed in U.S. Ser. Nos. 586,533 and 689,616, which are incorporated herein by reference.

As will be appreciated by those skilled in the art, the aminocarbamates of this invention are mixtures of many individual compounds.

The alkyl group will typically have a variety of carbon numbers since the starting olefins are not generally pure compounds and, for any given carbon number in the alkyl group, there are many structural isomers. Moreover, mono- and dialkyl phenols are generally obtained. Also, the number of propylene oxide units is an average number and different molecules will have a somewhat different number of PO units.

Also included within the scope of this invention are fully formulated lubricating oils containing a dispersant effective amount of an alkylphenyl poly(oxyalkylene) aminocarbamate.

Contained in the fully formulated composition is:
1. an alkenyl succinimide,
2. a Group II metal salt of a dihydrocarbyl dithiophosphoric acid,
3. a neutral or overbased alkali or alkaline earth metal hydrocarbyl sulfonate or mixtures thereof, and
4. a neutral or overbased alkali or alkaline earth metal alkylated phenate or mixtures thereof.
5. A viscosity index (VI) improver.

The alkenyl succinimide is present to act as a dispersant and prevent formation of deposits formed during operation of the engine. The alkenyl succinimides are well-known in the art. The alkenyl succinimides are the reaction product of a polyolefin polymer-substituted succinic anhydride with an amine, preferably a polyalkylene polyamine. The polyolefin polymersubstituted succinic anhydrides are obtained by reaction of a polyolefin polymer or a derivative thereof with maleic anhydride. The sUccinic anhydride thus obtained is reacted with the amine compound. The preparation of the alkenyl succinimides has been described many times in the art. See, for example, U.S. Pat. Nos. 3,390,082; 3,219,666; and 3,172,892, the disclosure of which are incorporated herein by reference. Reduction of the alkenyl substituted succinic anhydride yields the corresponding alkyl derivative. The alkyl succinimides are intended to be included within the scope of the term "alkenyl succinimide". A product comprising predominantly mono or bis-succinimide can be prepared by controlling the molar ratios of the reactants. Thus, for example, if one mole of amine is reacted with one mole of the alkenyl or alkyl substituted succinic anhydride, a predominantly mono-succinimide product will be prepared. If two moles of the succinic anhydride are reacted per mole of polyamine, a bis-succinimide will be prepared.

Particularly good results are obtained with the lubricating oil compositions of this invention when the alkenyl succinimide is a polyisobutene-substituted succinic anhydride of a polyalkylene polyamine.

The polyisobutene from which the polyisobutene-substituted succinic anhydride is obtained by polymerizing isobutene can vary widely in its compositions. The average number of carbon atoms can range from 30 or less to 250 or more, with a resulting number average molecular weight of about 400 or less to 3,000 or more. Preferably, the average number of carbon atoms per polyisobutene molecule will range from about 50 to about 100 with the polyisobutenes having a number average molecular weight of about 600 to about 1,500. More preferably, the average number of carbon atoms per polyisobutene molecule ranges from about 60 to about 90, and the number average molecular weight ranges from about 800 to 1,300. The polyisobutene is reacted with maleic anhydride according to well-known procedures to yield the polyisobutene-substituted succinic anhydride.

In preparing the alkenyl succinimide, the substituted succinic anhydride is reacted with a polyalkylene polyamine to yield the corresponding succinimide. Each alkylene radical of the polyalkylene polyamine usually has up to about 8 carbon atoms. The number of alkylene radicals can range up to about 8. The alkylene radical is exemplified by ethylene, propylene, butylene, trimethylene, tetramethylene, pentamethylene, hexamethylene, octamethylene, etc. The number of amino groups generally, but not necessarily, is one greater than the number of alkylene radicals present in the amine, i.e., if a polyalkylene polyamine contains 3 alkylene radicals, it will usually contain 4 amino radicals. The number of amino radicals can range up to about 9. Preferably, the alkylene radical contains from about 2 to about 4 carbon atoms and all amine groups are primary or secondary. In this case, the number of amine groups exceeds the number of alkylene groups by 1. Preferably the polyalkylene polyamine contains from 3 to 5 amine groups. Specific examples of the polyalkylene polyamines include ethylenediamine, diethylenetriamine, triethylenetetramine, propylenediamine, tripropylenetetramine, tetraethylenepentamine, trimethylenediamine, pentaethylenehexamine, di-(trimethylene)triamine, tri(hexamethylene)tetramine, etc.

Other amines suitable for preparing the alkenyl succinimide useful in this invention include the cyclic amines such as piperazine, morpholine and dipiperazines.

Preferably the alkenyl succinimides used in the compositions of this invention have the following formula:

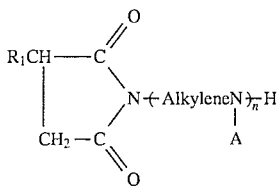

wherein:

a. $R_1$ represents an alkenyl group, preferably a substantially saturated hydrocarbon prepared by polymerizing aliphatic monoolefins. Preferably $R_1$ is prepared from isobutene and has an average number of carbon atoms and a number average molecular weight as described above;

b. the "Alkylene" radical represents a substantially hydrocarbyl group containing up to about 8 carbon atoms and preferably containing from about 2–4 carbon atoms as described hereinabove;

c. A represents a hydrocarbyl group, an amine-substituted hydrocarbyl group, or hydrogen. The hydrocarbyl group and the amine-substituted hydrocarbyl groups are generally the alkyl and amino-substituted alkyl analogs of the alkylene radicals described above. Preferably A represents hydrogen;

d. n represents an integer of from about 1 to 10, and preferably from about 3–5.

Also, included within the term "alkenyl succinimide" are the modified succinmides which are disclosed in U.S. Pat. No. 4,612,132 which is incorporated herein by reference.

The alkenyl succinimide is present in the lubricating oil compositions of the invention in an amount effective to act as a dispersant and prevent the deposit of contaminants formed in the oil during operation of the engine. The amount of alkenyl succinimide can range from about 1 percent to about 20 percent weight of the total lubricating oil composition. Preferably the amount of alkenyl succinimide present in the lubricating oil composition of the invention ranges from about 1 to about 10 percent by weight of the total composition.

The alkali or alkaline earth metal hydrocarbyl sulfonates may be either petroleum sulfonate, synthetically alkylated aromatic sulfonates, or aliphatic sulfonates such as those derived from polyisobutylene. One of the more important functions of the sulfonates is to act as a detergent and dispersant. These sulfonates are well-known in the art. The hydrocarbyl group must have a sufficient number of carbon atoms to render the sulfonate molecule oil soluble. Preferably, the hydrocarbyl portion has at least 20 carbon atoms and may be aromatic or aliphatic, but is usually alkylaromatic. Most preferred for use are calcium, magnesium or barium sulfonates which are aromatic in character.

Certain sulfonates are typically prepared by sulfonating a petroleum fraction having aromatic groups, usually mono- or dialkylbenzene groups, and then forming the metal salt of the sulfonic acid material. Other feedstocks used for preparing these sulfonates include synthetically alkylated benzenes and aliphatic hydrocarbons prepared by polymerizing a mono or diolefin, for example, a polyisobutenyl group prepared by polymerizing isobutene. The metallic salts are formed directly or by metathesis using well-known procedures.

The sulfonates may be neutral or overbased having base numbers up to about 400 or more. Carbon dioxide and calcium hydroxide or oxide are the most commonly used material to produce the basic or overbased sulfonates. Mixtures of neutral and overbased sulfonates may be used. The sulfonates are ordinarily used so as to provide from 0.3% to 10% by weight of the total composition. Preferably, the neutral sulfonates are present from 0.4% to 5% by weight of the total composition and the overbased sulfonates are present from 0.3% to 3% by weight of the total composition.

The phenates for use in this invention are those conventional products which are the alkali or alkaline earth metal salts of alkylated phenols. One of the functions of the phenates is to act as a detergent and dispersant. Among other things, it prevents the deposition of contaminants formed during high temperature operation of the engine. The phenols may be mono or polyalkylated.

The alkyl portion of the alkyl phenate is present to lend oil solubility to the phenate. The alkyl portion can be obtained from naturally occurring or synthetic sources. Naturally occurring sources include petroleum hydrocarbons such as white oil and wax. Being derived from petroleum, the hydrocarbon moiety is a mixture of different hydrocarbyl groups, the specific composition of which depends upon the particular oil stock which was used as a starting material. Suitable synthetic sources include various commercially available alkenes and alkane derivatives which, when reacted with the phenol, yield an alkylphenol. Suitable radicals obtained include butyl, hexyl, octyl, decyl, dodecyl, hexadecyl, eicosyl, tricontyl, and the like. Other suitable synthetic sources of the alkyl radical include olefin polymers such as polypropylene, polybutylene, polyisobutylene and the like.

The alkyl group can be straight-chained or branch-chained, saturated or unsaturated (if unsaturated, preferably containing not more than 2 and generally not more than 1 site of olefinic unsaturation). The alkyl radicals will generally contain from 4 to 30 carbon atoms. Generally when the phenol is monoalkyl-substituted, the alkyl radical should contain at least 8 carbon atoms. The phenate may be sulfurized if desired. It may be either neutral or overbased and if overbased will have a base number of up to 200 to 300 or more. Mixtures of neutral and overbased phenates may be used.

The phenates are ordinarily present in the oil to provide from 0.2% to 27% by weight of the total composition. Preferably, the neutral phenates are present from 0.2% to 9% by weight of the total composition and the overbased phenates are present from 0.2 to 13% by weight of the total composition. Most preferably, the overbased phenates are present from 0.2% to 5% by weight of the total composition. Preferred metals are calcium, magnesium, strontium or barium.

The sulfurized alkaline earth metal alkyl phenates are preferred. These salts are obtained by a variety of processes such as treating the neutralization product of an alkaline earth metal base and an alkylphenol with sulfur. Conveniently the sulfur, in elemental form, is added to the neutralization product and reacted at elevated temperatures to produce the sulfurized alkaline earth metal alkyl phenate.

If more alkaline earth metal base were added during the neutralization reaction than was necessary to neutralize the phenol, a basic sulfurized alkaline earth metal alkyl phenate is obtained. See, for example, the process of Walker et al, U.S. Pat. No. 2,680,096. Additional basicity can be obtained by adding carbon dioxide to the basic sulfurized alkaline earth metal alkyl phenate. The excess alkaline earth metal base can be added subsequent to the sulfurization step but is conveniently added at the same time as the alkaline earth metal base is added to neutralize the phenol.

Carbon dioxide and calcium hydroxide or oxide are the most commonly used material to produce the basic or "overbased" phenates. A process wherein basic sulfurized alkaline earth metal alkylphenates are produced by adding carbon dioxide is shown in Hanneman, U.S. Pat. No. 3,178,368.

The Group II metal salts of dihydrocarbyl dithiophosphoric acids exhibit wear, antioxidant and thermal stability properties. Group II metal salts of phosphorodithioic acids have been described previously. See, for example, U.S. Pat. No. 3,390,080, columns 6 and 7, wherein these compounds and their preparation are described generally. Suitably, the Group II metal salts of the dihydrocarbyl dithiophosphoric acids useful in the lubricating oil composition of this invention contain from about 4 to about 12 carbon atoms in each of the hydrocarbyl radicals and may be the same or different and may be aromatic, alkyl or cycloalkyl. Preferred hydrocarbyl groups are alkyl groups containing from 4 to 8 carbon atoms and are represented by butyl, isobutyl, sec.-butyl, hexyl, isohexyl, octyl, 2-ethylhexyl and the like. The metals suitable for forming these salts include barium, calcium, strontium, zinc and cadmium, of which zinc is preferred.

Preferably, the Group II metal salt of a dihydrocarbyl dithiophosphoric acid has the following formula:

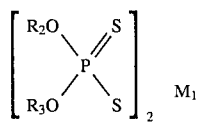

wherein:
- e. $R_2$ and $R_3$ each independently represent hydrocarbyl radicals as described above, and
- f. $M_1$ represents a Group II metal cation as described above.

The dithiophosphoric salt is present in the lubricating oil compositions of this invention in an amount effective to inhibit wear and oxidation of the lubricating oil. The amount ranges from about 0.1 to about 4 percent by weight of the total composition. Preferably, the salt is present in an amount ranging from about 0.2 to about 2.5 percent by weight of the total lubricating oil composition. The final lubricating oil composition will ordinarily contain 0.025 to 0.25% by weight phosphorus and preferably 0.05 to 0.15% by weight.

Viscosity index (VI) improvers are either non-dispersant or dispersant VI improvers. Non-dispersant VI improvers are typically hydrocarbyl polymers including copolymers and terpolymers. Typically hydrocarbyl copolymers are copolymers of ethylene and propylene. Such non-dispersant VI improvers a re disclosed in U.S. Pat. Nos. 2,700,633; 2,726,231; 2,7 92,288; 2,933,480; 3,000,866; 3,063,973; and 3,093,621 which are incorporated herein by reference for their teaching of non-dispersant VI improvers.

Dispersant VI improvers can be prepared by functionalizing non-dispersant VI improvers. For example, non-dispersant hydrocarbyl copolymer and terpolymer VI improvers can be functionalized to produce aminated oxidized VI improvers having dispersant properties and a number average molecular weight of from 1,500 to 20,000. Such functionalized dispersant VI improvers are disclosed in U.S. Pat. Nos. 3,864,268; 3,769,216; 3,326,804 and 3,316,177 which are incorporated herein by reference for their teaching of such dispersant VI improvers.

Other dispersant VI improvers include amine-grafted acrylic polymers and copolymers wherein one monomer contains at least one amino group. Typical compositions are described in British Patent No. 1,488,382; and U.S. Pat. Nos. 4,89,794 and 4,025,452, which are incorporated herein by reference for their teaching of such dispersant VI improvers.

Non-dispersant and dispersant VI improvers are generally employed at from 5 to 20 percent by weight in the lubricating oil composition.

Fuel Compositions

The alkylphenyl poly(oxypropylene) aminocarbamates of this invention will generally be employed in a hydrocarbon distillate fuel. The proper concentration of this additive necessary in order to achieve the desired detergency and dispersancy varies depending upon the type of fuel employed, the presence of other detergents, dispersants and other additives, etc. Generally, however, from 30 to 5,000 weight parts per million (ppm), and preferably 100 to 500 ppm and more preferably 200 to 300 ppm of alkylphenyl poly(oxypropylene) aminocarbamate per part of base fuel is needed to achieve the best results. When other detergents are present, a less amount of alkylphenyl poly(oxypropylene) aminocarbamate may be used. For performance as a carburetor detergent only, lower concentrations, for example 30 to 70 ppm may be preferred. Higher concentrations, i.e., 2,000 to 5,000 ppm may result in a clean-up effect on combustion chamber deposits.

The deposit control additive may also be formulated as a concentrate, using an inert stable oleophilic organic solvent boiling in the range of about 150° to 400° F. Preferably, an aliphatic or an aromatic hydrocarbon solvent is used, such as benzene, toluene, xylene or higher-boiling aromatics or aromatic thinners. Aliphatic alcohols of about 3 to 8 carbon atoms, such as isopropanol, isobutylcarbinol, n-butanol and the like, in combination with hydrocarbon solvents, are also suitable for use with the detergent-dispersant additive. In the concentrate, the amount of the additive will be ordinarily at least 5 percent by weight and generally not exceed 50 percent by weight, preferably from 10 to 30 weight percent.

When employing certain of the alkylphenyl poly(oxypropylene) aminocarbamates of this invention, particularly those having more than 1 basic nitrogen, it can be desirable to additionally add a demulsifier to the gasoline or diesel fuel composition. These demulsifiers are generally added at from 1 to 15 ppm in the fuel composition. Suitable demulsifiers include for instance L-1562®, a high molecular weight glycol capped phenol available from Petrolite Corp., Tretolite Division, St. Louis, Mo., and OLOA 2503Z®, available from Chevron Chemical Company, San Ramon, Calif.

In gasoline fuels, other fuel additives may also be included such as antiknock agents, e.g., methylcyclopentadienyl manganese tricarbonyl, tetramethyl or tetraethyl lead, or other dispersants or detergents such as various substituted succinimides, amines, etc. Also included may be lead scavengers such as aryl halides, e.g., dichlorobenzene or alkyl halides, e.g., ethylene dibromide. Additionally, antioxidants, metal deactivators and demulsifiers may be present.

In diesel fuels, other well-known additives can be employed such as pour point depressants, flow improvers, cetane improvers, etc.

Lubricating Oil Compositions

The alkylphenyl poly(oxypropylene) aminocarbamates of this invention are useful as dispersant additives when employed in lubricating oils. When employed in this manner, the additive is usually present in from 0.2 to 10 percent by weight to the total composition, preferably at about 0.5 to 8 percent by weight and more preferably at about 1 to 6 percent by weight. The lubricating oil used with the additive compositions of this invention may be mineral oil or synthetic oils of lubricating viscosity and preferably suitable for use in the crankcase of an internal combustion engine. Crankcase lubricating oils ordinarily have a viscosity of about 1300 CSt 0° F. to 22.7 CSt at 210° F. (99° C.). The lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_6$ to $C_{12}$ alpha olefins such as 1-decene trimer. Likewise, alkyl benzenes of proper viscosity such as didodecyl benzene, can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono and dicarboxylic acid and mono and dihydroxy alkanols can also be used.

Blends of hydrocarbon oils with synthetic oils are also useful. For example, blends of 10 to 25 weight percent hydrogenated 1-decene trimer with 75 to 90 weight percent 150 SUS (100° F.) mineral oil gives an excellent lubricating oil base.

Additive concentrates are also included within the scope of this invention. The concentrates of this invention usually include from about 90 to 50 weight percent of an oil of lubricating viscosity and from about 10 to 50 weight percent of the additive of this invention. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions. Suitable lubricating oils which can be used as diluents typically have viscosities in the range from about 35 to about 500 Saybolt Universal Seconds (SUS) at 100° F. (38° C.), although an oil of lubricating viscosity may be used.

Other additives which may be present in the formulation include rust inhibitors, foam inhibitors, corrosion inhibitors, metal deactivators, pour point depressants, antioxidants, and a variety of other well-known additives.

The following examples are offered to specifically illustrate this invention. These examples and illustrations are not to be construed in any way as limiting the scope of this invention.

EXAMPLES

Example A

Preparation of Alpha-Olefin Oligomers ($C_{14}$ -Derived) Using a Sulfonic Acid Catalyst This example shows alpha-olefin oligomers useful in this invention. Into a dry 500-ml, three-necked round bottom flask, equipped with a heating mantle, a mechanical stirrer, and a condenser were charged 200 grams of $C_{14}$ alpha olefin (Chevron Chemical Co., San Ramon, Calif.) and 10 grams of an experimental alumina-supported fluorosulfonic acid catalyst (DOW XUS 40036.07), available from Dow Chemical Company. These ingredients were heated and stirred under nitrogen for 25 hrs. at 185° C. At this time, the dark reaction mixture was stripped of any residual $C_{14}$ impurities by heating under vacuum, and then filtered. The product was analyzed by SFC, thus revealing a 95/5 ratio of olefin dimer to trimer. This product was used for phenol alkylation without further purification. This product could not be induced to crystallize at very low temperatures, and as such was regarded as wax free.

Example B

Preparation of Alpha-Olefin Oligomers ($C_{14}$-Derived) Using $BF_3$

This example also shows alpha-olefin oligomers useful in this invention. In this example, the $C_{14}$ alpha-olefin of Example A was oligomerized using boron trifluoride gas and an alcohol co-catalyst, as described, for example, in U.S. Pat. Nos. 4,238,343 and 4,045,507. Approximately 2½ gallons of a clear light yellow liquid containing approximately 67% dimer, 25% trimer, and 8% tetramer/pentamer combined were prepared. This mixture, having an average molecular weight of 472, was converted to the pinwheel alkyl phenol without further purification. This product was a nonviscous liquid at room temperature and below and was, as such, regarded as wax free.

Example C

Preparation of Alpha-Olefin Oligomers ($C_{16}$-Derived)

This example shows oligomers useful in this invention. The procedure of Example A was followed using a $C_{16}$ alpha olefin. The resulting product was an approximately 95/5 mixture of dimers to trimers. This product was a nonviscous liquid at room temperature and below and was, as such, regarded as wax free.

Example 1A

Preparation of Pinwheel Alkyl Phenols from ($C_{14}$-Derived) Oligomers of Example B Into a one-liter, three-necked flask, equipped with a heating mantle, mechanical stirrer, and condenser was charged 310 grams (0.66 mole) of the $BF_3$ prepared olefin oligomers of Example B. The liquid was heated to 85° C. at which time 344 grams (3.83 mole) of liquefied phenol was added followed by 65 grams of dry Amberlist 15. The reaction mixture was then heated for 24 hours at 150° C. at which time the resin was removed by hot suction filtration. Excess phenol was removed by vacuum distillation thus affording 343 grams of a non-viscous amber colored pinwheel alkyl phenol (343 grams; Hydroxyl number=105.4). This phenol had an average alkyl carbon content of 36 carbon atoms. This product was converted to polyoxypropylene alcohol without further purification. This phenol was a nonviscous liquid at room temperature and became a thick oil at lower temperature. No waxing was observed.

Example 1B

Preparation of Pinwheel Alkyl Phenols from Oligomers of Example C

The $C_{16}$-derived olefin oligomer of Example C was used to alkylate phenol in a manner similar to that described in Example 1A. The resulting pinwheel alkyl phenol had an average alkyl carbon content of 34 carbon atoms.

Example 1C (Comparative)

Preparation of a $C_{20}$–$C_{24}$ Terminal Alkylphenol

To a 5-liter flask, equipped with stirrer, Dean Stark trap, condensor, and nitrogen inlet and outlet was added 500 gm of a substantially straight chain $C_{20}$ to $C_{24}$ alpha olefin mixture (approximate olefin content $C_{18}$ and less-1%; $C_{20}$-49%; $C_{22}$-42%; $C_{24}$-8%; $C_{26}$ and greater-0.1%) wherein in the entire olefin fraction at least 15 mole percent of said olefins contain vinylidine groups ($C_{20}$ to $C_{24}$ alpha olefins are available from Chevron Chemical Company, San Ramon, Calif.), 656 grams of phenol and 75 grams of a sulfonic acid cation exchange resin (polystyrene crosslinked with divinylbenzene) catalyst (Amberlyst 15® available from Rohm and Haas, Philadelphia, Pa.). The reaction mixture was stripped by heating under vacuum and the product was filtered hot over diatomaceous earth to afford 1050 grams of a $C_{20}$ to $C_{24}$ terminal alkylphenol with a hydroxyl number of 120 (i.e. mg KOH/gm sample) and with approximate 45% para-alkylphenol content. This phenol was a low melting wax at room temperature.

Example 2A (Comparative)

Preparation of a $C_{20}$–$C_{28}$ Terminal Alkylphenol

To a 2-liter flask, equipped with stirrer, Dean Stark trap, condensor and nitrogen inlet and outlet was added 674 gms of a substantially straight chain $C_{20}$ to $C_{28}$ alpha olefin mixture (olefin content: $C_{18}$-2%; $C_{20}$-28%; $C_{22}$-19%; $C_{24}$-13%; $C_{26}$-21%; $C_{28}$-11%; and greater than $C_{30}$-6%) wherein in the entire olefin fraction at least 20 mole percent of said olefins contain vinylidine groups ($C_{20}$–$C_{24}$ alpha olefins and $C_{24}$–$C_{28}$ alpha olefins are available from Chevron Chemical Company, San Ramon, Calif. and are then physically mixed at an equal mole basis to provide a $C_{20}$–$C_{28}$ olefin mixture), 211.5 grams of phenol, 43 grams of a sulfonic acid cation exchange resin (polystyrene crosslinked with divinylbenzene) catalyst (Amberlyst 15® available from Rohm and Haas, Philadelphia, Pa.). The reaction mixture was heated to about 140° C. for about 8 hours with stirring under a nitrogen atmosphere. The reaction mixture was stripped by heating under vacuum and the product was filtered hot over diatomaceous earth to afford 574 grams of a $C_{20}$–$C_{28}$ alkylphenol with a hydroxyl number of 110 and with 56% para-alkylphenol content. This alkylphenol had approximately 26% dialkyl phenol and had an average alkyl carbon number of 29. This product was a hard wax at room temperature.

Example 2B (Comparative)

Preparation of Low Dialkyl $C_{20\text{-}28}$ Terminal Alkyl Phenol

The procedure of Example 2A was used except 966 gm of $C_{20}$–$C_{28}$ alpha olefins and 211.5 gm of phenol were used. The resulting alkyl phenol had approximately 6% dialkyl phenol and an average alkyl carbon number of 24. This product was a wax at room temperature.

Example 2C (Comparative)

Preparation of a $C_{26}$-Average Terminal Alkyl Phenol

In a separate procedure, the low dialkyl $C_{20\text{-}28}$ phenol of Example 2B was realkylated using an additional 10% of $C_{20}$–$C_{24}$ alpha olefin (per conditions described in Example 1C). This reaction thus afforded an alkylphenol composed of approximately 16% dialkyl phenol species. The average alkyl carbon number was 26. This product was a wax at room temperature.

Example 3 (Comparative)

Preparation of Tetrapropenylphenol

To a 2-liter flask, equipped with stirrer, Dean Stark trap, condensor, and nitrogen inlet and outlet was added 567 grams of tetrapropylene, 540 grams of phenol, 72 grams of a sulfonic acid cation exchange resin (polystyrene crosslinked with divinylbenzene) catalyst (Amberlyst 15® available from Rohm and Haas, Philadelphia, Pa.). The reaction mixture was heated to about 110° C. for about 3 hours with stirring under a nitrogen atmosphere.

The reaction mixture was stripped by heating under vacuum and the resulting product filtered hot over diatomaceous earth to afford 626 grams of tetrapropenylphenol and with a hydroxyl number of 205 and with 96% para-alkylphenol content.

Example 4 (Comparative)

Preparation of $C_{20}$ to $C_{28}$ Terminal Alkylphenol Poly(oxypropylene) Alcohol To a dried 12-liter 3-necked flask under a nitrogen atmosphere was added 3.5 liters of toluene and 2020.5 grams (4.61 moles) of a $C_{20}$ to $C_{28}$ terminal alkylphenol prepared in a manner similar to Example 2A. The system was warmed to approximately 60° C. and 60 grams (1.54 moles) of metallic potassium cut into small pieces was slowly added with vigorous stirring. The temperature of the reaction system was allowed to increase during this addition and reached approximately 100° C. After 2½ hours, all of the metallic potassium was dissolved. The reaction system was then allowed to cool to 60° C. Afterwards, 4552 grams (78.37 moles) of propylene oxide was added to the system by an addition funnel at an addition rate slow enough to avoid flooding of the vapor condensing system. The system was then gently refluxed for 72 hours at which point the temperature increased to 110° C. and was held there for an additional 3 hours. The system was then cooled to 60° C. and the reaction quenched by the addition of 0.54 liter of 3N HCl solution. The system was then dried by azeotropic distillation. The system was then diluted with 10 liters of hexane which was afterwards extracted three times with a slightly basic brine solution (pH≈8 to 9). In each extraction, a cuff between the aqueous solution and the hexane solution was formed. The cuff as well as the aqueous solution was discarded after each extraction. The resulting hexane solution was stripped and dried under elevated temperature and high vacuum to afford 4450 grams of the title compound as a light weight oil having a molecular weight of approximately 1435 and a hydroxyl number of 39. The product had an average of 17 PO units. This procedure was repeated to give the product listed as Example 13 below. This product was a waxy paste at room temperature.

Example 5A (Comparative)

Preparation of $C_{20}$ to $C_{28}$ Terminal Alkylphenyl Poly(oxypropylene) Chloroformate To a 12-liter 3-necked flask under a nitrogen atmosphere was added 3 liters of anhydrous toluene and 3042 grams (2.6 moles) of $C_{20}$ to $C_{28}$ terminal alkylphenyl poly(oxypropylene) alcohol prepared as in Example 4 above. The system was cooled to 5° C. with stirring. While stirring, grams (3.0 moles) of liquid phosgene was added all at once to the reaction system. The reaction system was allowed to warm to room temperature and stirred gently for hours. In order to remove excess phosgene as well as HCl formed during the reaction, the system was vigorously sparged with nitrogen. Infrared analysis of an aliquot revealed a strong chloroformate absorption at 1785 cm$^{-1}$ and no detectable alcohol absorption at 3450 cm$^{-1}$. This product was a waxy paste at room temperature.

Example 5B

Preparation of a Pinwheel Alkylphenyl Poly(oxypropylene) Chloroformate from the Poly(oxypropylene) Alcohol of Example 32

To a cooled (5° C.) mechanically stirred solution of the pinwheel poly(oxypropylene) alcohol (440 grams, 0.26 moles) of Example 32, derived from $C_{14}$ oligomer, in 1 liter of dry toluene under a nitrogen atmosphere was added all at once 254 ml of a 20% solution of phosgene in toluene (242 grams). The reaction mixture was allowed to warm to room temperature and stirred gently for 24 hours to remove excess phosgene and the HCl formed during the reaction period. Infrared analysis of an aliquot revealed a strong chloroformate absorption at 1785 cm$^{-1}$ and no detectable alcohol (3450 cm$^{-1}$). This product was a liquid at room temperature.

Example 6 (Comparative)

Preparation of $C_{20}$ to $C_{28}$ Alkylphenyl Poly(oxypropylene) Ethylene Diamine (EDA) Carbamate The entire chloroformate/toluene solution of Example 5A was diluted with 4 liters of dry toluene. In a separate flask, 2565 grams (42.7 moles) ethylene diamine (EDA) was also diluted with 4 liters of dry toluene. At room temperature, these two solution were rapidly mixed using two variable speed teflon gear pumps and a 10 inch Kenics static mixer. After fifteen minutes, the crude reaction mixture was stripped, diluted with 12 liters of hexane, washed successively once with water and three times with a slightly basic (pH≈9) brine solution. Phase separation of the aqueous brine solution and the hexane solution was improved by adding brine as needed. The hexane solution was separated, dried over anhydrous sodium sulfate, filtered and stripped to afford the title product as a light yellow liquid which solidified to a loose paste upon cooling and having an alkalinity value of 30 and 0.75 weight percent basic nitrogen. This preparation was repeated to give the product listed as Example 23 below. This product was a waxy paste at room temperature and did not pass the wax test as described in Example 45.

Example 7 (Comparative)

Preparation of $C_{20}$ to $C_{28}$ Terminal Alkylphenyl Poly(oxypropylene) Diethylene Triamine Carbamate In the manner described in Example 6 above, 2256 grams (1.53 moles) of $C_{20}$ to $C_{28}$ terminal alkylphenyl poly(oxypropylene) chloroformate prepared similarly to method described in Example 5A above was treated with 2654 grams (25.8 moles) of diethylene triamine (DETA) to afford the title compound having an alkalinity value of 56 and 1.4 weight percent basic nitrogen. This preparation was repeated to give the product listed as Example 27 below. This product was a waxy paste at room temperature and failed the wax test of Example 45.

Example 8 (Comparative)

Preparation of n-Butyl poly(oxypropylene) Ethylene Diamine Carbamate 2000 grams (0.91 moles) of n-butyl poly(oxypropylene) alcohol was prepared in the manner of Example 4 by substituting n-butanol for the $C_{20}$ to $C_{28}$ alkylphenol. The n-butyl poly(oxypropylene) alcohol was then treated with phosgene in the manner of Example 5A to yield the n-butyl poly(oxypropylene) chloroformate which was reacted with 1093 grams (18.2 moles) of ethylene diamine in the manner of Example 6 to yield the title compound as a light yellow liquid having an alkalinity value of 22.5 and 0.56 weight percent basic nitrogen. This product was a liquid at room temperature and passed the wax test of Example 45.

Examples 9–17 (Comparative)

Other hydrocarbyl poly(oxyalkylene) alcohols were prepared by employing different hydrocarbyl groups including those of Examples 2A and 3; by employing different poly(oxyalkylene) groups of different chain lengths. Examples 9 through 17 are found below in Table I, which summarizes the different hydrocarbyl poly(oxyalkylene) alcohols so prepared.

TABLE I

POLY(OXYALKYLENE) ALCOHOLS OF THE FORMULA $$R_3-O+(CH_2CHO)_n H$$
$$\quad\quad\quad\quad\quad | $$
$$\quad\quad\quad\quad R_1$$

| Ex. | $R_3$ | Phenol Source Ex. No. | $R_1$ | n | Avg. No. of Alkyl Carbons |
|---|---|---|---|---|---|
| 9 | n-butyl | — | $-CH_3$ | ~37 | 4 |
| 10 | n-butyl | — | $-CH_3$ | ~23 | 4 |
| 11 | tetrapropenyl-phenyl | 3 | $-CH_3$ | ~20 | 12 |
| 12 | tetrapropenyl-phenyl | 3 | $-CH_2CH_3$ | ~17 | 12 |
| 13 | $C_{20-28}$ terminal alkylphenyl | 2A | $-CH_3$ | ~17 | 29 |
| 14 | $C_{20-28}$ terminal alkylphenyl | 2A | $-CH_3$ | ~14 | 29 |
| 15 | $C_{20-28}$ terminal alkylphenyl | 2A | $-CH_3$ | ~10 | 29 |
| 16 | $C_{20-28}$ terminal alkylphenyl | 2A | $-CH_3$ | ~6 | 29 |
| 17 | $C_{20-28}$ terminal alkylphenyl | 2A | $-CH_2CH_3$ | ~17 | 29 |
| 29 | $C_{20-28}$ terminal alkylphenyl | 2B | $-CH_3$ | ~17 | 24 |
| 30 | $C_{20-28}$ terminal alkylphenyl | 2B | $-CH_3$ | ~13 | 24 |
| 31 | $C_{20-28}$ terminal alkylphenyl | 2C | $-CH_3$ | ~14 | 26 |
| 32 | α-$C_{14}$ oligomer | 1A | $-CH_3$ | ~20 | 36 |

TABLE I-continued

POLY(OXYALKYLENE) ALCOHOLS OF THE FORMULA $$R_3-O+CH_2CHO)_{\overline{n}}H$$
$$\qquad\quad\; |\phantom{+CH_2CHO)}R_1$$

| Ex. | $R_3$ | Phenol Source Ex. No. | $R_1$ | n | Avg. No. of Alkyl Carbons |
|---|---|---|---|---|---|
| 33 | α-$C_{14}$ oligomer derived alkylphenyl | 1A | $-CH_3$ | ~16 | 36 |
| 34 | α-$C_{16}$ oligomer derived alkylphenyl | 1B | $-CH_3$ | ~17 | 34 |

TABLE II

Carbamates of the Formula $$R_3O+CH_2CHO)_{\overline{n}}CNH+CH_2-CH_2-NH)_{\overline{p}}H$$
$$\qquad\quad\;\; |\phantom{+CH_2CHO)_n}\|$$
$$\qquad\quad\;\; R_1\phantom{+CH_2CHO)_nCNH+}O$$

| Ex. | $R_3$ | Phenol Source Ex. No. | $R_1$ | n | p | Avg. No. of Alkyl Carbons |
|---|---|---|---|---|---|---|
| 18 | n-butyl | — | $-CH_3$ | ~37 | 1 | 4 |
| 19 | n-butyl | — | $-CH_3$ | ~23 | 1 | 4 |
| 20 | tetrapropenylphenyl | 3 | $-CH_3$ | ~20 | 1 | 12 |
| 21 | tetrapropenylphenyl | 3 | $-C_2H_5$ | ~17 | 1 | 12 |
| 22 | tetrapropenylphenyl | 3 | $-C_2H5$ | ~17 | 2 | 12 |
| 23 | $C_{20-28}$ terminal alkylphenyl | 2A | $-CH_3$ | ~17 | 1 | 29 |
| 24 | $C_{20-28}$ terminal alkylphenyl | 2A | $-CH_3$ | ~14 | 1 | 29 |
| 25 | $C_{20-28}$ terminal alkylphenyl | 2A | $-CH_3$ | ~10 | 1 | 29 |
| 26 | $C_{20-28}$ terminal alkylphenyl | 2A | $-CH_3$ | ~6 | 1 | 29 |
| 27 | $C_{20-28}$ terminal alkylphenyl | 2A | $-CH_3$ | ~17 | 2 | 29 |
| 28 | $C_{20-28}$ terminal alkylphenyl | 2A | $-CH_3$ | ~17 | 1 | 29 |
| 35 | $C_{20-28}$ terminal alkylphenyl | 2B | $-CH_3$ | ~17 | 1 | 24 |
| 36 | $C_{20-28}$ terminal alkylphenyl | 2B | $-CH_3$ | ~13 | 1 | 24 |
| 37 | $C_{20-28}$ terminal alkylphenyl | 2B | $-CH_3$ | ~13 | 2 | 24 |
| 38 | $C_{20-28}$ terminal alkylphenyl | 2C | $-CH_3$ | ~14 | 1 | 26 |
| 39 | α-$C_{14}$ oligomer derived pinwheel alkylphenyl | 1A | $-CH_3$ | ~20 | 2 | 36 |
| 40 | α-$C_{14}$ oligomer derived pinwheel alkylphenyl | 1A | $-CH_3$ | ~16 | 2 | 36 |
| 41 | α-$C_{14}$ oligomer derived pinwheel alkylphenyl | 1A | $-CH_3$ | ~17 | 2 | 34 |

Examples 18–28 (Comparative)

Other hydrocarbyl poly(oxyalkylene) aminocarbamates were prepared by employing different hydrocarbyl groups including those of Examples 2 and 3 and by employing poly(oxyalkylene) groups of different chain lengths. Examples 18 through 28 are found in Table II, which summarizes the different hydrocarbyl poly(oxyalkylene) aminocarbamates so prepared.

Example 29 (Comparative)

Preparation of a $C_{24}$ Terminal AlkylPhenyl Poly(oxypropylene) Alcohol

In a manner similar to that described in Example 4, 622 gm (1.45 moles) of the terminal low dialkyl terminal phenol derived from the $C_{20}$ to $C_{28}$ alpha olefin (Example 2B) was converted to 2048 gm of the poly(oxypropylene) alcohol (Hydroxyl number=40.0; average molecular weight=1402) by reaction with approximately 17 moles of propylene oxide. This product was a waxy paste at room temperature.

Example 30 (Comparative)

Preparation of a $C_{24}$ Average Terminal Alkylphenyl Poly(oxypropylene) Alcohol The alkyl phenol of Example 2B was reacted with 13 moles of PO in the manner of Example 4 to give the alkylphenyl poly(oxypropylene) alcohol of the example.

Example 31 (Comparative)

Preparation of a $C_{26}$ Terminal Alkyl Phenyl Poly(oxypropylene) Alcohol

The alkyl phenol of Example 2C was converted to a 14 PO unit polymer (as determined by NMR) in a manner similar to that described in Example 4, but using 14 moles of propylene oxide per mole of phenol. This product was a waxy paste at room temperature.

Example 32

Preparation of Pinwheel Poly(oxypropylene) Alcohols from $C_{14}$ Oligomer Derived Phenol of Example 1A This experiment was carried out in dry 2-liter, three-necked flask, equipped with a heating mantle, mechanical stirrer, and a dry ice condenser fitted to maintain an inert nitrogen atmosphere. To a warm solution of dry toluene (250 ml) and 203 grams (0.36 moles) of the pinwheel alkylphenol of Example 1A was slowly added potassium metal (5.4 gr) in small pieces with vigorous mechanical stirring. The pot temperature increased to approximately 100° C. during the addition, and after 2½ hours, all of the potassium was dissolved. After cooling to 60° C., 585 mls of propylene oxide (486 grams, 8.36 moles) was added in such a way as to avoid flooding of the vapor condensing system. The reaction solution was gently refluxed for 72 hours at which point the temperature rose to 110° C. and was held at temperature for an additional 3 hours. After cooling to 60° C., the reaction was quenched with 60 ml of 3N HCl (a slight excess) and dried by azeotropic distillation. The crude product was then diluted with hexane (3 liters), extracted three times with slightly basic brine. In each case, a cuff was formed and discarded. The resulting hexane solution was then stripped and dried under high vacuum to afford 670 gr of a light yellow oil having a molecular weight of approximately 1725 (by hydroxyl number determination). Spectroscopic analysis ($^1H$ and $^{13}C$ NMR) revealed that this alcohol contained an average of propylene oxide monomer units. This product was a nonviscous liquid at room temperature and could not be induced to crystallize at low temperature.

Example 33

Preparation of Pinwheel Alkylphenyl Poly(oxypropylene) Alcohols

The pinwheel alkyl phenol of example 1A ($C_{14}$-derived) was converted to the poly(oxypropylene) alcohol by reaction with 16 mole equivalents of propylene oxide in a manner similar to that described in Example 32.

Example 34

Preparation of Pinwheel Alkylphenyl Poly(oxypropylene) Alcohols

The pinwheel alkyl phenol of example 1B ($C_{16}$-derived) was converted to the poly(oxypropylene) alcohol by reaction with 17 mole equivalents of propylene oxide in a manner similar to that described in Example 32.

Example 35 (Comparative)

Preparation of the Terminal Low Dialkyl $C_{20-24}$ Carbamate EDA

Without further purification, the terminal alkylphenol alcohol of Example 29 was converted to the chloroformate as described in Example 5A, except that a 20 weight percent solution of phosgene in toluene was employed rather than condensed phosgene liquid (for handling convenience and safety). After reaction, the chloroformate was then vigorously sparged to remove excess phosgene and the HCl reaction by-product.

The resulting chloroformate was then converted to the corresponding EDA carbamate by reaction with ethylene diamine as described in Example 6. The average alkyl carbon number was 24; alkalinity value=34; basic nitrogen was 0.85%. This product did not pass the wax test of Example 45.

Sequence V-D engine testing as described in Example 43 revealed that varnish control was exceedingly poor (4.4, average of three separate tests). In an effort to improve this performance aspect, a similar molecule was synthesized, but with less propylene oxide units. This is shown in Example 36.

Example 36 (Comparative)

Preparation of a Terminal $C_{24}$-Average Alkyl Phenyl Poly(oxypropylene) EDA Carbamate In a separate procedure, the terminal low dialkyl $C_{20-28}$ alkylphenol of Example 2B was converted to a phenol-capped poly(oxypropylene) alcohol containing 13 propylene oxide units using a procedure similar to that described in Example 4. This alcohol was converted to the corresponding chloroformate, as in Example 5A using a phosgene/toluene solution. The chloroformate was degassed and used without further purification.

One portion of this chloroformate was converted to an EDA carbamate as in Example 6 (alkalinity value=37, 0.93% basic nitrogen). This product did not pass the wax test of Example 45.

Example 37 (Comparative)

Preparation of a $C_{24}$ Terminal Alkylphenyl Poly(oxypropylene) DETA Carbamate The remainder of the chloroformate of Example 36 was converted to the corresponding DETA carbamate (alkalinity value=67.4, 1.69% basic nitrogen) as in Example 7. This product did not pass the wax test of Example 45.

Example 38 (Comparative)

Preparation of a $C_{24}$-Average Terminal Alkylphenyl Poly(oxypropylene) EDA Carbamate The poly(oxypropylene) alcohol of Example 31 was converted to the corresponding chloroformate as in Example 5A and reacted with EDA to afford the desired ethylene diamine carbamate in a manner similar to that of Example 6 (alkalinity value=34.0, 0.85% basic nitrogen). This product did not pass the wax test of Example 45.

As demonstrated by Examples 24, 35, 36, 37, and 38, reducing the number of propylene oxide units in the additive backbone does not improve varnish performance nearly as significantly as does increasing the number of alkyl carbons in the alkyl phenol. As can be seen in Example 35, an average alkyl carbon content of 24 carbon atoms with PO formulations is insufficient to provide the required varnish and sludge control. Neither by reducing the PO content (Example 36) nor by switching to DETA carbamates (Example 37) can varnish performance be restored to the level exemplified by Example 24. However, by increasing the dialkyl content to a higher level (Example 38), performance is restored to base case values. None of these examples, however, represents a total solution to the overall problem which additionally requires these additives to be nonwaxy at low temperatures, thus passing the test of Example 45.

Example 39

Preparation of Alkylphenyl Poly(oxypropylene) Diethylenetriamine Carbamate

The chloroformate/toluene solution of Example 5B was diluted to 2 liters with dry toluene. In a separate flask, 530 grams of diethylene triamine (5.2 moles) was also diluted to 2 liters with dry toluene. These two solutions were rapidly mixed using two variable speed teflon gear pumps and a 10-inch Kenics static mixer. The crude reaction mixture was then stripped, diluted with 6 liters of hexane, and washed successively with water (4×), basic (pH=9) water (2×), and water (4×). Phase separation was improved by adding isopropanol as needed. The organic layer was then dried over anhydrous $NaSO_4$, filtered and stripped to afford a light orange product which remained a liquid at −40° C. (alkalinity value=50, 1.25% basic nitrogen). As such, this product was regarded as non-waxy by virtue of passing the wax test of Example 45. This carbamate does not produce detrimental varnish and sludge relative to the base oil.

Examples 40–41

Preparation of Aminocarbamates of the Present Invention

The pinwheel alcohols 33 and 34 were reacted in a manner similar to Examples 5 and 7 to give a $C_{14}$-oligomer derived DETA pinwheel carbamate having 16 propylene oxide units and an average alkyl carbon number of 34 (Example 40) and a $C_{16}$-oligomer derived DETA pinwheel carbamate having 17 propylene oxide units and an average alkyl carbon number of 36 (Example 41). These products pass the wax test at –40° C. and do not produce detrimental sludge or varnish relative to base oil.

Example 42

Oil Solubility Bench Test

This procedure was designed to determine the oil solubility/compatibility of different additives in a fully formulated lubricating oil. Insofar as as much as 25–30% of a gasoline additive can enter into the crankcase via blow-by and/or cylinder wall/piston ring "wipe down", this is an important performance criteria.

The lubricating oil composition was formulated to contain: 6 percent by weight of a mono-polyisobutenyl succinimide; 20 millimoles per kilogram of a highly overbased sulfurized calcium phenate; 30 millimoles per kilogram of a highly overbased sulfurized calcium hydrocarbyl sulfonate; 22.5 millimoles per kilogram of a zinc dithiophosphate; 13 weight percent of a commercial non-dispersant viscosity index improver; 5 parts per million of a foam inhibitor in 150N Exxon base oil to give a 10 W 40 formulated oil. The oil solubility of the additive was determined as follows:

To a heated solution (50 grams) of the above-described lube oil was added 50 grams of the neat additive. The mixture was then heated with constant stirring to 170° F. and maintained at that temperature for 15 minutes. Dilutions were then prepared according to the desired solubility test range using fresh hot reference oil as the diluent. In each case, the diluted samples were stirred to 170° F. for 10 minutes to insure complete mixing. The solutions were then sealed and left to cool undisturbed for from 1–5 days typically at room temperature. Each sample was then rated visually for oil continuity.

Additives that were marginally soluble in this blend separated as a denser secondary phase, and were clearly visible as such without the need for centrifugation. Additives which gave rise to oil incompatibility problems were inherently oil soluble, however, they tended to displace what appears to be the VI (viscosity index) improver. This phenomenon resulted in the separation of the VI improver which is less dense than the bulk oil forming a clear thick upper layer. The solubility/compatibility of a gasoline additive was thereby defined as the highest concentration (on a weight basis) which did not result in the formation of either an insoluble lower additive phase or an insoluble upper VI improver phase.

The oil solubility (or insolubility) of the hydrocarbyl poly(oxyalkylene) aminocarbamates including the alkylphenyl poly(oxypropylene) aminocarbamates of this invention is believed to correlate well to the oil solubility of the precursor hydrocarbyl poly(oxyalkylene) alcohol.

Accordingly, Table III below contains solubility data for the hydrocarbyl poly(oxyalkylene) alcohols. Oil solubility is reported in weight percent of additive in the lubricating oil composition.

TABLE III

| Example No | Oil Solubility |
|---|---|
| 9 | 5 |
| 10 | 8 |
| 11 | 18 |
| 12 | 27 |
| 13 | 40 |
| 14 | 50 |
| 15 | 50 |
| 16 | 50 |
| 17 | 50 |

The oil solubility of the aminocarbamates is reported in Table III.

Example 43

Sequence V-D Test Method

Formulated oils containing alkylphenyl poly(oxypropylene) aminocarbamate were tested in a Sequence V-D test method as well as formulated oils containing comparative hydrocarbyl poly(oxyalkylene) aminocarbamates. This procedure utilizes a Ford 2.3-liter, four-cylinder Pinto engine. The test method simulates a type of severe field test service characterized by a combination of low speed, low temperature "stop and go" city driving and moderate turnpike operation. The effectiveness of the additives in the oil is measured in terms of the protection against sludge and varnish deposits on a 0 to 10 scale with 0 being black and 10 indicating no varnish or sludge deposits. The results of these tests are found in Table IV below.

The reference composition was formulated to contain: 6 percent by weight of a mono-polyisobutenyl succinimide; 20 millimoles per kilogram of a highly overbased sulfurized calcium phenate; 30 millimoles per kilogram of a highly overbased calcium hydrocarbyl sulfonate; 22.5 millimoles per kilogram of a zinc dithiophosphate; 13 weight percent of a commercial non-dispersant viscosity index improver; 5 parts per million of a foam inhibitor in 150N Exxon base oil to give a 10 W 40 formulated oil.

Comparisons against this reference were made by employing an oil formulated identically as the reference except for the additional amount of the additive as shown in Table IV below:

TABLE IV

Carbamate Performance and Properties

| Ex. | Oil (a) Compatibility | Wax (b) at −40° C. | Crankcase (c) Av. Varnish 2.5 (d) | 5.5 | Crankcase Av. Sludge 2.5 | 5.4 | Av.(e) HC No. |
|---|---|---|---|---|---|---|---|
| 18 | 0.5 | no |  | 4.4 |  | 9.2 | 4 |
| 19 | 1 | no |  |  |  |  | 4 |
| 20 | 7 | no |  |  |  |  | 12 |
| 21 | 15 | no | 5.7 | 5.5 | 9.5 | 9.55 | 12 |
| 22 | 15 | no |  |  |  |  | 12 |
| 23 | 16 | yes |  |  |  |  | 29 |
| 24 | 20 | yes | 6.4 | 7.5 | 9.6 | 9.35 | 29 |
| 25 | 45 | yes |  |  |  |  | 29 |
| 26 | 50 | yes |  |  |  |  | 29 |
| 27 | 16 | yes |  |  |  |  | 29 |
| 28 | 16 | yes |  |  |  |  | 29 |
| 35 | 18 | yes |  | 4.4 |  | 9.5 | 24 |
| 36 | 20 | yes |  | 5.4 |  | 9.4 | 24 |
| 37 | 18 | yes |  | 7.4 |  | 9.2 | 24 |
| 38 | 22 | yes |  | 6.2 |  | 9.4 | 26 |
| 39 | 18 | no |  | (f) |  | (f) | 34 |
| 40 | 18 | no |  | (f) |  | (f) | 36 |
| 41 | 18 | no |  | (f) |  | (f) | 34 |

(a) See Ex. 42
(b) See Ex. 45
(c) See Ex. 43 - Rating scale = 1–10, with 10 meaning no varnish or sludge.
(d) Weight percent additive.
(e) Average alkyl carbon number in alkyl phenyl group
(f) These carbamates are not detrimental relative to the base oil of Example 30.

Examples 18 through 22 represent previously known hydrocarbyl poly(oxyalkylene) aminocarbamates. This Table establishes that the alkylphenyl poly(oxypropylene) aminocarbamates of this invention (Examples 39–41) were less detrimental, i.e. gave decreased crankcase deposits, as measured by average varnish in the Sequence V-D results.

The table also establishes that the additives of this invention possess lubricating oil compatibility. This is particularly surprising in view of the fact that previously known hydrocarbyl poly(oxypropylene) aminocarbamates are not lubricating oil compatible, i.e., Examples 18, 19 and 20.

Example 44

TGA Stability of Aminocarbamates

The thermal oxidative stability of fuel additives can be measured by thermogravimetric analysis (TGA). The TGA procedure employed Du Pont 951 TGA instrumentation coupled with a microcomputer for data analysis. Samples of the fuel additives, approximately 25 milligrams, were heated isothermally at 200° C. under air flowing at 100 cubic centimeters per minute. The weight of the sample was monitored as a function of time. Incremental weight loss is considered to be a first order process. Kinetic data, i.e., rate constants and half-lives, were readily determined from the accumulated TGA data. The half-life measured by this procedure represents the time it takes for half of the additive to decompose and evaporate. Half-life data for a fuel additive correlates to the likelihood that that additive will contribute to ORI. Lower half-lives represent a more easily decomposable product one which will not as likely accumulate and form deposits in the combustion chamber. All of the comparative carbamate examples and the carbamate examples of the present invention have good TGA performance, i.e. half lives of less than about 4 hours, and therefore will contribute minimally to ORI.

Example 45

Determination of Additive Waxiness

Since it is not unusual for solutions of these additives to be subjected to cold temperature extremes, it is important that solids (typically waxy) are not formed during handling, storage, or in actual field use. When formed, these waxy constituents can totally plug the in-line filtering devices normally in service in additive distribution systems and the fuel or lube systems of actual operating engines. Such a plugging would obviously be catastrophic and must be avoided. The following test procedure constitutes a reasonable evaluation of this low temperature tendency and serves as the critical distinguishing feature of this invention whereby propylene oxide oligomers are to be employed as dispersants/detergents.

The test additive (30 grams) is dissolved in an equivalent weight of reagent grade toluene, cooled to −40° C., and held at that temperature for four weeks. The sample solution is then inspected for visual clarity ("brightness"). If any sedimented solids appear or the sample is hazy, the sample has failed the test. A sample which passes this test is one described as "clear and bright", a well-known industry-designated standard.

Example 46

Measuring the Epoxide Content

NMR spectroscopy provides a method for measuring the backbone "epoxide content" of these additives. The ether carbons and their associated protons are segregated and easily "counted".

The "epoxide count", independently determined from carbon and proton NMR spectra is averaged and gives good repeatability and consistent agreement with our experimental charge mole ratios and reaction mass balance data.

Analysis of the polyethers can be done at the alcohol stage or later on in the products.

Analyses were performed using a Varian VXR-300. The polyethers were dissolved "as is" in deuteromethylene chloride (30 mg/ml), and the proton FT NMR spectra was determined according to the instrument parameters detailed below.

For carbon FT NMR spectra, the polyethers were also dissolved in deuteromethylene chloride (400 mg/ml) which contained approximately 5 mg of a relaxation agent, Cr(III)-tris-acetylacetonate, i.e., Cr(III)(AcAc)$_3$. All spectra were determined using high performance 5 mm NMR tubes.

Instrument Conditions

|  | To Observe Proton | To Observe Carbon |
|---|---|---|
| Frequency | 299.944 MHz | 75.429 MHz |
| Spectral Width | 5000 Hz | 20492 Hz |
| Acq. Time | 1.6 Sec | 0.4 Sec |
| Relax. Delay | 2.0 Sec | 2.0 Sec |
| Pulse Width | 14° | 90° |
| Temperature | Ambient | Ambient |
| No. Repetitions | 16 | 2048 |
| Spin Rate | 20 Hz | 24 Hz |
| FT Size | 16K | 32K |

Determination of Integral Values

Proton NMR Spectra

The aromatic protons, observed in the range of 6.5 to 7.5 ppm, serve as the internal standard for this evaluation. When dealing with products derived from "high dialkylation" phenols (20 to 25%), the integral value for this region of the spectra is divided by 3.75. This signal value per proton is then used to evaluate ether carbon proton content. Otherwise, this signal is attributed to four aryl protons (for phenols having <10% dialkylation).

The ether protons of interest lie in the region between 3.2 and 4.0 ppm. Here we see the mass of methylene and methine protons which include the separated multiplets observed for the first and the last epoxide units assembled in these polyethers. One-half of the total number of propylene oxide (PO) related protons are observed in this region, whereas only three-eighths of the butylene oxide (BO)-related protons are represented here.

Carbon NMR Spectra

The six aromatic carbons, observed in the range of 105 to 160 ppm, serve as the internal standard for this evaluation. This is no need to make any allowances for the presence of dialkyl phenol in this case.

The ether carbons of interest lie in the region between 60 and 80 ppm. Bearing in mind that only two-thirds of the observable PO-related carbons are counted in this region (one-half for BO polymers), the calculation to determine epoxide units is straightforward.

Example 47

Determination of the Nature of the Alkylphenyl Group

Analytical methods for determining the general nature of the alkylphenyl substituent of the aminocarbamates can be accomplished in the following manner:

A sample of an alkylphenyl poly(oxyalkylene) aminocarbamate (identified by Infrared and NMR spectroscopy) is hydrolyzed using strong base to afford the corresponding polyoxyalkylene alcohol. Further non-oxidative thermal degradation strips away the polyether portions leaving behind the alkyl phenol. This residue can then be examined by Mass Spectroscopy for the appearance of the tropylium ion species. Alkyl phenols tend to fragment in such a way that the larger of the two (or three) benzylic substituents will be eliminated in the formation of the observed phenol ion species. Thus, the tropylium ions generated from simple alpha olefins will typically contain from 1–3 carbon atoms more than those accounted for by the aromatic ring itself. By comparison, the same ionized species generated from the pinwheel alkyl phenols employed in the invention, such as those derived from an alpha olefin oligomer, will contain many more carbon atoms due to fragmentation at the benzylic positions.

It is important to recognize that such tropylium ion species are readily formed from alkyl phenols, and high energy impact ionization may be too severe a technique for all cases. As a result, under forcing conditions, more detailed information concerning the structure of the alkyl portion may be lost. In these cases, it is possible to examine "low energy" impact ionization which may be useful for observing these tropylium ions. In any event, tropylium ions are noted for their relative stability and more often than not appear as the base ion peak (peak of highest relative intensity). See: Silverstein, Basslet, and Morril, *Spectrometric Identification of Organic Compounds*. Wiley and Sons (New York, 1974) pp. 19–22.

Another less preferred but supporting analysis can be performed by conducting carefully controlled oxidations of the alkyl phenol side chains. This is typically done via aqueous potassium permanganate oxidation under pH conditions designed to control the extent of the oxidative chain cleavage reactions desired. If the alkyl phenol has been derived by alkylation with, for example, linear alpha olefins, then a bimodal distribution of low and high molecular weight alkanoic acids will result. However, if the phenol in question is a pinwheel alkyl phenol and the phenyl ring is attached toward the center of the alkyl chain, then higher molecular weight alkanoic acids will be observed, although they may not comprise the majority of oxidation reaction products. Hence, for a pinwheel alkyl phenol derived from a $C_{10}$ α-olefin oligomer, one would expect to observe the corresponding $C_7$–$C_9$ alkanoic acids after degradation. On the other hand, when the phenol derived from simple $C_{20}$ alpha olefin alkylation is examined, high molecular weight acid fragments will also be produced and observed which will reflect the existence of these longer chains in the original phenol.

It should be noted that due to the general severity of these reaction conditions, one may observe only small quantities of these heavier acids. However, by derivatization they may be observed chromatographically. In concert with other general data such as phenol molecular weight, dialkylation level, etc. this method can be informative.

Example 48

Determination of Average Alkyl Hydrocarbon Content of Alkylphenols

Chemical Method

After determining the hydroxyl number (mg KOH/gr sample) for a given phenol, the molecular weight is calculated: MW=56,100/hydroxyl number, wherein 56,100 is the milliequivalent weight of KOH.

Since the phenol portion of these products accounts for 91 mass units, the balance (MW–91) is due to the average alkyl hydrocarbon content.

As these alkyl groups are saturated hydrocarbons, dividing the balance portion by 14 (the mass units for a —CH$_2$— moiety) gives the average number of alkyl hydrocarbon atoms in the phenol.

Spectroscopic Method

Alternatively, NMR analysis can be used to determine the average alkyl hydrocarbon content. NMR analysis of integrated $^1$H spectra indicate the relative balance of aryl to aliphatic hydrogens which can be used to approximate the average hydrocarbon content of the phenol.

This information may also be obtained by using integrated $^{13}$C NMR spectra of these products. Thus, the number of aromatic carbons can be used as an internal standard for gauging the average number of saturated carbons in the phenol. Typically, the $^1$H and $^{13}$C NMR results are averaged and are in good agreement with the chemical determination.

It is assumed that the average alkyl hydrocarbon content of the phenols does not change during the reaction to make the alcohols, chloroformates and carbamates.

What is claimed is:

1. A wax-free liquid alkylphenol wherein the alkyl group is a substantially straight-chain alkyl group of from about 25 to 50 carbon atoms and is attached to the phenol ring at least 6 carbon atoms from the terminus of the longest chain of the alkyl group, and wherein the alkyl group comprises at least two hydrocarbon tails of at least 6 carbon atoms in length, and further wherein the alkyl group is derived from a substantially straight-chain alpha olefin oligomer of $C_8$ to $C_{20}$ alpha olefins.

2. An alkylphenol according to claim 1, wherein the alkyl group contains from about 28 to 50 carbon atoms.

3. An alkylphenol according to claim 2, wherein the alkyl group contains from about 30 to 45 carbon atoms.

4. An alkylphenol according to claim 1 wherein the alkyl group is derived from a substantially straight-chain alpha olefin oligomer of $C_{10}$ to $C_{16}$ alpha olefins.

5. An alkylphenol according to claim 1, wherein the alkyl group is derived from a substantially straight-chain alpha olefin oligomer selected from the group consisting of $C_8$ tetramers, $C_{10}$ trimers, $C_{12}$ trimers, $C_{14}$ dimers and trimers, $C_{16}$ dimers and trimers, $C_{18}$ dimers and $C_{20}$ dimers.

* * * * *